United States Patent
Zolla-Pazner et al.

(10) Patent No.: US 7,847,085 B2
(45) Date of Patent: Dec. 7, 2010

(54) RECOMBINANT HIV-1 GP120 IMMUNOGEN WITH THREE DIFFERENT V3 LOOPS FROM VIRUSES OF DIFFERENT CLADES

(75) Inventors: Susan Zolla-Pazner, New York, NY (US); Shan Lu, Hopkinton, MA (US); Shixia Wang, Northborough, MA (US)

(73) Assignees: New York University, New York City, NY (US); The University of Massachusetts, Boston, MA (US)

( * ) Notice: Subject to any disclaimer, the term of this patent is extended or adjusted under 35 U.S.C. 154(b) by 324 days.

(21) Appl. No.: 11/772,760

(22) Filed: Jul. 2, 2007

(65) Prior Publication Data

US 2008/0095791 A1 Apr. 24, 2008

(51) Int. Cl.
*C07H 21/04* (2006.01)
*A61K 39/21* (2006.01)

(52) U.S. Cl. .................. 536/23.72; 536/23.4; 424/188.1
(58) Field of Classification Search ........................ None
See application file for complete search history.

(56) References Cited

PUBLICATIONS

Liang et al., Epitope insertion into variable loops of HIV-1 gp120 as a potential means to improve immunogenicity of viral envelope protein, Vaccine, 1999, 17:2862-2872.*
Gomez et al., Efficient CD8+ T cell response to the HIV-env V3 loop epitope from multiple virus isolates by a DNA prime/vaccinia virus boost (rWR and rMVA strains) immunization regime and enhancement by the cytokine IFN-γ, Virus Research, 2004, 105:11-22.*
Andre et al., Increased Immune Response Elicited by DNA Vaccination with a Synthetic gp120 Sequence with Optimized Codon Usage, Journal of Virology, 1998, 72(2):1497-1503.*
Arnold, GF et al., "Broad Neutralization of Human Immunodeficiency Virus Type 1 (HIV-1) Elicited from Human Rhinoviruses That Display the HIV-1 gp41 ELDKWA Epitope," J. Virol. 83:5087-5100 (2009) = supplemental Table 1.

* cited by examiner

*Primary Examiner*—Zachariah Lucas
*Assistant Examiner*—Nicole Kinsey White
(74) *Attorney, Agent, or Firm*—Browdy and Neimark, PLLC

(57) ABSTRACT

A novel immunogenic HIV-1 Env, particularly gp120, DNA construct is disclosed in which either the V1/V2 loop and the V4 loop, or all three variable loops, including V3, are replaced with a V3 sequence each of which is from a different viral isolate. Preferably, each replacement V3 loop is a consensus sequence of V3 of a different clade. Such constructs are useful as immunogens as each presents three independent V3 epitopes, so that the immunized subject generates a more broadly reactive neutralizing antibody response than with conventional gp120 or V3 DNA or polypeptide immunogens. Also disclosed are methods of using the DNA construct to immunize a mammal, preferably a human, particularly in a priming regiment in which the DNA immunogen is followed by administration of a V3 fusion protein boosting immunogen.

43 Claims, 1 Drawing Sheet

RECOMBINANT HIV-1 GP120 IMMUNOGEN WITH THREE DIFFERENT V3 LOOPS FROM VIRUSES OF DIFFERENT CLADES

BACKGROUND OF THE INVENTION

1. Field of the Invention

The invention in the field of biochemistry and medicine relates to improved chimeric HIV envelope protein (Env) immunogen or vaccine compositions in which an Env-encoding nucleic acid includes three different Env V3 loop sequences.

2. Description of the Background Art

The strains of HIV-1 can be classified into three groups: the "major" group M, the "outlier" group 0 and the "new" group N. These three groups may have resulted from three separate introductions of simian immunodeficiency virus into humans. Group 0 appears to be restricted to west-central Africa and group N—discovered in 1998 in Cameroon—is extremely rare. More than 90% of HIV-1 infections belong to HIV-1 group M. Within group M there are known to be at least nine genetically distinct clades or subtypes of HIV-1: clades A, B, C, D, F, G, H, J and K.

Occasionally, two viruses of different subtypes can meet in the cell of an infected person and mix together their genetic material to create a new hybrid virus. Many of these new strains do not survive for long, but those that infect more than one person are known as "circulating recombinant forms" or CRFs. For example, the CRF A/E is a mixture of genes in one virus from clades A and E.

The classification of HIV strains into lades and CRFs is complex, and the definitions are subject to change as new discoveries are made. Some scientists refer to clades or subtypes A1, A2, A3, F1 and F2 instead of A and F, though others regard the former as sub-clades or sub-subtypes.

Many HIV-1 neutralizing antibodies in infected individuals or in immunized animals are directed against the V3 loop of the viral envelope protein gp120 which was accordingly designated the principal neutralizing determinant of HIV-1 (Rusche, J R et al (1988) *Proc. Natl. Acad. Sci. USA* 85: 3198-3202). HIV-neutralizing antibodies against V3 are thought to prevent the binding of gp120 to either R5 or X4 co-receptors, thus abolishing fusion of the virus with its target cell.

The present inventors and colleagues developed the human mAb 447-52D (IgG3, λ) from a heterohybridoma derived from peripheral blood mononuclear cells of a clade B HIV-1-infected individual (Gorny, M K et al. (1993) *J. Immunol.* 150, 635-643). Monoclonal antibody 447-52D is one of the most broadly neutralizing and most potent anti-V3 antibodies that has been studied to date. It binds to intact virions from clades A, B, C, D, F, G and H (Nyambi, P N et al. (1998) *J. Virol.* 72, 9384-9391) and neutralizes primary isolates from several clades, including both X4 and R5 type viruses (Cecilia, D et al. (1998) *J. Virol.* 72.6988-6996; Conley, A J et al. (1994) *J. Virol.* 68.6994-7000; Fouts, T R et al. (1997) *J. Virol.* 71:2779-2785; Gorny, M K et al. (2002) *J. Virol.* 76:9035-9045; Hioe, C E et al. (1997) *Int. Immunol.* 9:1281-1290; Nyambi et al., supra; Verrier, F et al. (2001) *J. Virol.* 75:9177-9186). 447-52D recognizes the V3 loop; its core epitope has been mapped with overlapping peptides to the highly conserved motif at the V3 crown GPxR (residues 319-322) (Gorny M K et al. (1992) *J. Virol.* 66:7538-7542; Gorny et al., 1993, supra). Unlike most anti-V3 antibodies, 447-52D can neutralize both X4 and R5 primary viral isolates correlating with its ability to bind V3 peptides with a wide range of sequence variability (Zolla-Pazner, S et al. (1999) *J Virol* 73:4042-4051. 447-42D binds to different V3 peptides with association constants ranging between $2 \times 10^5$ and $10^8$ M$^{-1}$, the highest of which is only one order of magnitude lower than its affinity for the corresponding (intact) gp120 protein (VanCott, T C et al. (1994) *J. Immunol.* 153:449-459). Since 447-52D was elicited during the course of a natural HIV-1 infection and neutralizes a broad spectrum of HIV-1 isolates, it is believed to recognize a native V3 conformation.

The presence of neutralizing antibodies in patient sera and the development of monoclonal antibodies such as the 447-52D demonstrates the ability of the human immune response to produce protective antibodies. However, the induction of broadly neutralizing anti-HIV-1 antibodies, more particularly broadly neutralizing anti-V3 antibodies, via immunization of animals and humans has largely been a haphazard matter of chance.

Recent attempts to produce broadly reactive neutralizing antibodies are described in several publications. Chakrabarti B K et al, 2005, *Vaccine* 23:3434-45, compared Env immunogens with substituted V3 regions to combinations of strains from different clades, evaluating the ability of such immunogens to expand the breadth of the neutralizing antibody response. When the V3 region from HIV BaL was substituted for HIV HXB2, an effective neutralizing antibody response against several clade B primary isolates was elicited, but remained restricted to neutralization of most clade B isolates. In an attempt to expand this response further, a linear epitope recognized by the broadly neutralizing 2F5 antibody was inserted into V3. A V3 epitope was identified that bound to Ab 2F5 and elicited a potent 2F5-like antibody response when administered as an immunogen. However such antisera neutralized only a lab-adapted strain and not primary isolates. In contrast, combinations of Envs from clades A, B, and C, elicited neutralizing antibodies to a more diverse group of primary HIV-1 isolates. The authors suggested that combinations of Env immunogens, despite the limited reactivity of the V3 from each component, can be used to expand the breadth of the neutralizing antibody response.

A multi-envelope HIV-1 vaccine cocktail, containing 51 unique envelope proteins has been tested in six macaques, giving rise to significant neutralization of viruses from clades A, B, and D (Zhan, X et al, 2005; *Vaccine* 23:5306-20. Epub 2005 Jul. 20). This vaccine was administered as successive immunizations with recombinant DNA, recombinant vaccinia virus and recombinant HIV-1 Env proteins. Following vaccination, animals developed diverse anti-Env antibodies with binding and neutralizing activities toward proteins and viruses that were not represented by sequences in the vaccine. Vaccinated and control animals were challenged with the heterologous pathogen SHIV, 89.6P. The vaccinated monkeys experienced significantly lower virus titers and better maintenance of CD4+ T-cells than did unvaccinated controls. Four of six vaccinated animals but only one of six control animals, survived 44-weeks post-challenge. The authors stated that this was the first report describing control of pathogenic SHIV disease by a heterologous HIV-1 vaccine (devoid of 89.6 or simian immunodeficiency virus derivatives).

Seaman M S, et al., 2005, *J Virol.* 79:2956-63, examined the magnitude and breadth of envelope (Env)-specific T-lymphocyte and antibody responses generated by vaccines containing either a single or multiple genetically distant HIV-1 Env immunogens. Rhesus monkeys were immunized with DNA prime-recombinant adenovirus boost vaccines encoding a Gag-Pol-Nef polyprotein in combination with either a single Env or a mixture of clade-A, clade-B, and clade-C Envs. Monkeys receiving the multiclade Env immunization developed robust immune responses to all vaccine antigens and, importantly, a greater breadth of Env recognition than monkeys immunized with vaccines including a single Env immunogen. All groups of vaccinated monkeys were infected following challenge with the pathogenic simian-human immunodeficiency virus 89.6P and demonstrated equivalent immune protection in terms of control of viremia. The authors suggested that a multicomponent vaccine encoding Env proteins from multiple clades of HIV-1 can generate broad Env-specific T-lymphocyte and antibody responses without antigenic interference and that it is possible to generate protective immune responses by vaccination with genetically diverse isolates of HIV-1.

In a recent publication by two of the present inventors (Lu and Wang) and their colleagues (Virology, e-published Apr. 6, 2006)), they compared polyvalent vs. monovalent immunization of rabbits. Polyvalent constructs gave better results. Rabbits were first immunized with a DNA vaccine expressing 1, 3 or 8 primary HIV-1 gp120 antigens delivered by gene gun followed by boosting with recombinant gp120 protein. Sera from rabbits immunized with DNA priming plus protein boosting, but not DNA vaccine alone or the Env protein alone, were capable of neutralizing 7 of 10 viruses in one type of assay and 12 of 14 viruses in a second type of assay. Sera from rabbits immunized with the polyvalent Env antigens neutralized a significantly higher percentage of viruses than did sera from rabbits immunized with monovalent antigens. The authors suggested that DNA priming followed by recombinant Env protein boosting can be used to deliver polyvalent Env-antigen-based HIV-1 vaccines to elicit neutralizing antibody responses against viruses with diverse genetic sequence variations.

In the Chakrabarti et al. study, above, the investigators used (i) a "monoclade" immunogen (500 µg of purified plasmid DNA from gp145deltaCFI of HIV-1 HXB2 substituted with the V3 of HTV-1 BAL) or (ii) a multiclade immunogen comprising three different preparations, so that "vaccinees" got 167 µg of each of three plasmids. In the latter case, it is noteworthy that only ⅓ the amount of each V3 epitope was administered, which would be expected to compromise the effort. The present invention differs fundamentally from the approach of Chakrabarti et al., Seaman et al. and Wang et al., supra, in that a single molecule carrying the three different V3 regions is administered, thereby providing to the vaccinee the full complement of each of three V3s.

Other than the few studies cited above, the polyvalent approach using Env antigens from different clades of primary HIV-1 isolates circulating in the world has not been well investigated. A number of difficulties in developing polyvalent Env vaccines are discussed briefly below:

(1) Screening and Selecting Multiple Antigens:

This has been approached in a variety of ways resulting in conflicting conclusions. For example, a report from one of the present inventors (Zolla-Pazner) and colleagues (Nyambi et al., 2000, J. Virol. 74:10670-80) suggested that little or no correlation exists between clade and antigenic characteristics of the HIV-1 gp120 envelope glycoprotein; rather, "immunotypes" were defined which include viruses from diverse clades carrying Env proteins with common antigenic characteristics In contrast, Binley, J M et al., 2004, J Virol. 78:13232-52, suggested that Env antigenic characteristics do correlate with clades. Still others have used an essentially random method of selecting large numbers of virus envelopes in the hopes of covering all or most of the possible virus subtypes. (See, for example Zhan et al., supra.)

(2) Producing Multiple Antigens:

If a polyvalent vaccine is needed, and if each immunogen is represented by a different molecule, the production, quality control and safety issues are multiplied by the number of molecules that will need to be combined into the vaccine.

(3) The Use of Multiple Immunogens May Weaken the Immune Response to Each:

This is exemplified by results of Wang et al., supra, in which a combination of 8 immunogens yielded a weaker immune response than a combination of three. The present inventors' approach disclosed herein is based on the reasoning that an immunogenic molecule that comprises, and can present, multiple copies of relevant antigen(s) would be advantageous as, in essence, such a molecule would introduce several moles of the epitope of interest per mole of immunogen.

(4) None of the Current Approaches Described Above Focus the Immune Response Exclusively to Epitopes that are Known to Induce Neutralizing Antibodies:

Thus, if one immunizes with one or multiple Env molecules as immunogens, the recipient will make antibodies to dozens of epitopes, and the majority of these will not be neutralizing antibodies. Only very few HIV-1 envelope glycoprotein epitopes induce neutralizing antibodies, one of these being V3.

SUMMARY OF THE INVENTION

Upon considering the issues and difficulties in the art discussed above, the present inventors conceived of the efficiency and utility of an immunogen that presents multiple copies of epitope(s) from diverse HIV-1 viruses on a single immunogenic molecule. This is a result of the present inventors quest for ways to design immunogens and immunization protocols to induce neutralizing antibodies with the highest possible titer and broadest profile of reactivity against the V3 loop epitope(s) of the HIV-1 Env protein gp120. Thus they sought to induce, in a predictable way, the production of more broadly reactive and neutralizing anti-V3 antibodies (such as, for example, the 447-52 antibody which recognized the GPGR tip of the V3 loop) that preferably are reactive with the V3 loops of more than a single HIV-1 clade. Such antibodies may also resemble the antibodies designated 3074, 2557, 2558, 3019, 2334 and 2601 that recognize the GPGQ tip of V3 (Krachmarov C P et al. J. Virol., in press; Gorny, M et al. J. Virol., to be published July 2006). Initial efforts involved have been directed to immunizing rabbits using a DNA vaccine encoding the gp120 protein to prime the animals and using a V3 fusion protein (V3-FP) to boost. A single gp120 protein has only one "copy" of the V3 loop peptide per molecule, and that V3 is limited to the sequence representative of a single clade (subtype) of HIV-1 virus.

The inventors conceived of a novel immunogenic gp120 DNA construct in which two additional loop regions, the V1/V2 loop and the V4 loop, are each replaced with a V3 sequence, preferably each from a different clade. Thus, each gp120-encoding DNA molecule being presented to the animal has three potentially independent copies of V3. Moreover, the three different V3 loops could be from different HIV-1 clades, for example clades A, B and C. Such a construct, referred to in abbreviated form as "gp120-ABC" will provide more V3-specific immunological memory and an antibody response of broader scope, as it can be directed ab initio against V3 epitopes of three different viral sources.

It should be appreciated that the present strategy can be used with any HIV Env protein, or DNA encoding such protein, as a vaccine construct. See, for example, Chakrabarti B K et al, 2002, *J Virol.* 76:5357-68; Burton D R et al, 2004, *Nat Immunol.* 5:233-6; Akahata W et al., 2005, *J Virol.* 79:626-31; Mascola J R et al., 2005, *J Virol.* 79:771-9; Nabel G J, 2005, *Science.* 308:1878-9. This includes gp160, the full length Env protein, the precursor of gp120, or any fragment of gp160 such as gp145 or gp140 or a mutant or deletion variant of the Env protein, such as deltaV2gp140 HIV-1 (deletion of 30 amino acids and one N-linked glycosylation site from the V2 loop). (See, for example, Stamatatos L et al., 1998, *J Virol.* 72:7840-5; Stamatatos L et al., 2000, AIDS Res Hum Retroviruses., 16:981-94; Cherpelis S et al., 2001, *J. Virol.* 75:1547-50; Barnett S W et al., 2001, *J Virol.* 75:5526-40; Cherpelis S et al., 2001, *Immunol Lett.* 79:47-55; Stamatatos L et al., 2001, *AIDS.* 15 *Suppl* 5:S105-15; Srivastava I K et al., 2003, *J Virol.* 77:2310-20; Srivastava I K et al., 2003, *J Virol* 77:11244-59; Haigwood N L et al., 2003, *AIDS* 17 Suppl 4:S67-71; Li M et al., 2005, *J Virol.* 79:10108-25; Xu R et al., 2006, Virology 349:276-89. Epub 2006 Mar. 9, 2006, all of which references are hereby incorporated by reference in their entirety.) Thus, the variable regions/loops of any of these Env protein constructs can be replaced as described herein, so that the present strategy is not limited to the gp120 protein per se.

In a preferred embodiment, the present invention provides a recombinant nucleic acid molecule that encodes a recombinant HIV-1 gp120 envelope protein which recombinant protein is useful as an immunogen for priming an antibody response to V3 epitopes of gp120, the nucleic molecule comprising a first and a second nucleotide sequence each encoding a gp120 V3 loop that is not native to a source gp120 protein wherein the first and second sequences replace the native V1/V2 and V4 loops of the source gp120 protein, wherein each of the first and second nucleotide sequences is different from the other, and encode two different V3 loop polypeptides with sequences of the same or distinct clades of HIV-1 that are also the same or distinct from the clade from which the source gp120 protein is obtained.

The above nucleic acid molecule preferably further comprises a third nucleotide sequence that encodes a third V3 loop which:
(a) is not native to, and is different in sequence from, the V3 loop of the source gp120 protein; and
(b) replaces the native V3 loop of the source gp120 protein in the encoded polypeptide.

These nucleic acid molecules are preferably in the form of DNA plasmids. However, the same coding sequences can be used for the production of recombinant Env proteins that include the same three V3 loops.

Preferred embodiments are expression vectors of the above nucleic acid molecules that comprise, operably linked to the sequence encoding recombinant gp120 envelope protein, a promoter, and optionally, expression control sequences that facilitate expression of the DNA in cells of the mammalian subjects to which such DNA molecules are administered to induce priming. Such promoters and expression control sequences are well-known in the art.

In the above nucleic acid molecule, each replacement V3 loop is preferably from an HIV-1 clade selected from the group consisting of clades A, B, C, D, E, F, G, H, I, J and K or a subclade of any of the clades. Each replacement V3 loop may encode the consensus amino acid sequence of, the V3 loop of an HIV-1 clade selected from the group consisting of clade A, B, C, D, E, F, G, H, I, J and K, or a subclade of any of the clades. As an example, the three replacement V3 loops are from clade A (e.g., subclade A1), B and C. Alternatively, the three V3 loops in this design can be from different HIV viral isolates of the same clade as long as the combination of more than one V3 loop in this design can expand the breadth of neutralizing antibodies against HIV infection.

In one embodiment, the source gp120 protein for the above nucleic acid molecule from a clade A virus, more preferably the isolate CA-1, as exemplified herein. However, the source gp120 can be from other HIV isolates of the same clade or isolates from other clades.

The above HIV env nucleic acid molecule preferably encodes a recombinant gp120 or other forms of HIV Env protein wherein the source gp120 variable loop sequences are replaced as follows:
(a) V1/V2 is replaced with a V3 loop sequence, more preferably the consensus V3 sequence, of sub-clade A1;
(b) V3 is replaced with a V3 loop sequence, more preferably the consensus V3 sequence, of clade B; and
(c) V4 is replaced with a V3 loop sequence, more preferably the consensus V3 sequence, of clade C.

The above nucleic acid molecule is preferably designed with different level of codon optimization to minimize the potential intra-DNA recombination as well as to achieve the optimal expression in the mammalian species in which it is to be used as a DNA immunogen or vaccine, for example, in mouse, rabbit, non-human primate or a human. The nucleic acid molecule may also be used for the production of recombinant HIV Env protein immunogen with an amino acid sequence corresponding to the optimized nucleotide sequence. Such recombinant HIV Env polypeptides have utility in research or in treatment of HIV infections.

The invention is also directed to an immunogenic pharmaceutical composition comprising the above nucleic acid molecule and an immunologically and pharmaceutically acceptable carrier or excipient.

The invention includes a method of immunizing a mammalian subject, preferably a human, to induce an immune response that is focused on V3 epitopes of the HIV-1 gp120 protein. The immunizing step comprises administering to the subject an immunogenically-effective amount of (a) the above nucleic acid molecule or (b) the above immunogenic pharmaceutical composition, to prime an the immune response that can be boosted by subsequent protein/peptide administration. The above subject may be a human who is susceptible to, or at risk of, HIV-1 infection, or one who is infected with HIV-1.

In the above method, the nucleic acid or the composition may be administered by needle-less jet injection, intradermal injection, intramuscular injection, or gene gun delivery.

The above method is one that results in a broadly neutralizing antibody response.

The invention is directed to a method for inducing a broadly neutralizing antibody response primarily directed to V3 epitopes of the HIV-1 gp120 protein, comprising:
(a) priming an immune response according to the above method; and
(b) administering one or more boosting doses of a boosting V3 immunogen, preferably a polypeptide or peptide immunogen, comprising V3 epitopes. The boosting immunogen may comprise the same or different V3 epitopes compared to the priming DNA immunogen. The boosting immunogen may be administered between 1 and 12 weeks after the priming, and the boosting step may be repeated more than one time.

The above method may further include administering an adjuvant or a facilitating agent before, during, or after priming, or in combination with protein/peptide boosting. Adjuvants or facilitating agents, including those that are preferably for human use, are well-known in the art.

In another embodiment, the invention is directed to a kit comprising the above nucleic acid molecule or pharmaceutical composition and instructions for administering the nucleic acid composition to a subject for priming an anti-V3 antibody response. The kit may further include a polypeptide or peptide molecule that comprises V3 epitopes, such as a V3 fusion protein, and instructions for administering the polypeptide or peptide to boost the anti-V3 antibody response. The kit may also include an adjuvant.

Also provided is a use of (a) a nucleic acid molecule as defined above, or (b) an immunogenic pharmaceutical composition as defined above for the manufacture of a medicament for priming a mammalian subject for an immune response against V3 epitopes of the HIV-1 gp120 polypeptide.

In another embodiment is provided a use as above, that further comprises use of a boosting V3 immunogen comprising the same V3 epitopes against which the priming is directed for the manufacture of a medicament for inducing a broadly neutralizing antibody response against V3 epitopes of the HIV-1 gp120 polypeptide. The boosting immunogen in this medicament is preferably a polypeptide or peptide immunogen that comprises said V3 epitopes. The boosting immunogen medicament is preferably administered between 1 and 12 weeks after priming.

In another embodiment is provided a use as defined above that further comprises use of an adjuvant or facilitating agent for the manufacture of the priming medicament, the boosting medicament or both, which medicament is for priming the indicated immune response or for inducing the broadly-reactive antibody response, wherein said adjuvant or facilitating agent is administered before, during, or after priming.

In the above uses, the mammalian subject in which the priming, boosting, and inducing the antibody response is preferably a rodent, a rabbit (or other lagomorph), a non-human primate, or a human.

DESCRIPTION OF THE PREFERRED EMBODIMENTS

Figure 1:
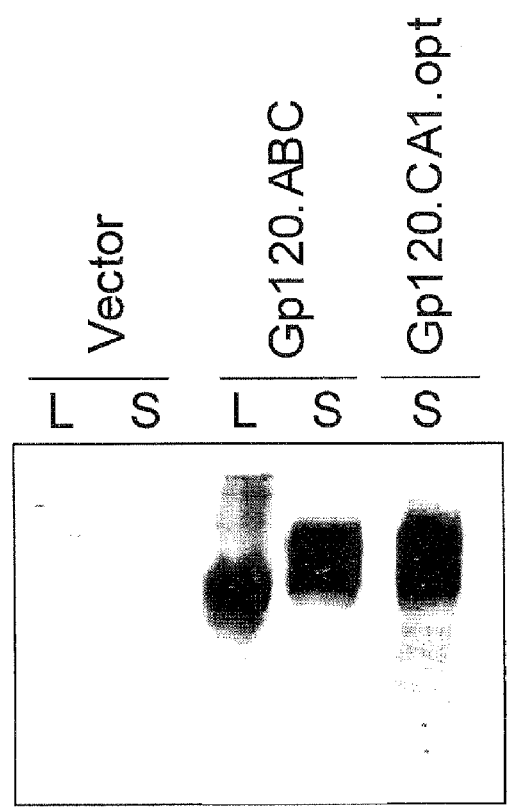
FIG. 1 shows a Western-blot analysis of "gp120.ABC" expression by DNA vaccine in transfected 293T cell lysate (L) and supernatant. "Vector"—the empty DNA vaccine vector as negative control; "Gp120.ABC"—the "gp120-ABC" DNA vaccine; "Gp120.CA1.opt"—codon optimized CA1 gp120 DNA vaccine as positive control.

The present invention is directed to novel immunogenic gp120 DNA constructs in which two additional loop regions, the V1/V2 loop and the V4 loop, are each replaced with a V3 sequence so that the DNA molecule encodes three potentially independent copies of HIV V3 region peptides. The three different V3 loops are preferably from different HIV-1 isolates or clades, for example clades A, B and C. As a result, such a construct serves as a DNA immunogen or vaccine that induces more potent V3-specific immunological memory and an antibody response of broader scope, directed against V3 epitopes of three different sources, as compared to immunogens of the prior art. More preferably, the immunogenic DNA molecule of the present invention is used to prime subjects to induce immunological memory. Subsequent administration of protein immunogens in any immunogenic form are used to evoke the enhanced immune response in such primed subjects.

Below is the nucleotide (SEQ ID NO: 1) and amino acid sequence (SEQ ID NO:2) of a gp120 referred to herein as "gp120-ABC" which is a chimeric sequence in which portions of the sequence of CA1 have been substituted. CA1 is a CRF13_cpx virus carrying a clade A env gene whose gp120 DNA was used for studies in rabbits (and which was chosen on the basis of previous work of the present inventors and their colleagues.

For studies in rabbits, this construct is codon-optimized for use in rabbits and rabbits are immunized with this DNA construct. For use in humans, the construct is codon-optimized for human expression. Codon-optimization is well-known in the art.

SEQ ID NO: 1, below is the wild type nucleotide sequence of gp120.CA1:

```
tgg gtc aca gtc tat tat ggg gta cct gtg tgg aga gat gca gat acc    48 act ctc ttt tgt gcg tct gat gct aaa gca tat agt act gaa aaa cat    96 aat gtc tgg gct aca cat gcc tgt gta ccc aca gac ccc gac cca caa   144 gag ata tat ctg gaa aat gta aca gaa aat ttt aac atg cgg aaa aat   192 aac atg gta gaa cag atg cat gag gat ata atc agt tta tgg gat gaa   240 agc cta aaa cca tgt gta aag cta acc cct ctc tgt gtt act tta aac   288 tgt act gat gta aag act aag aat aga act gtg gaa gac caa gca gaa   336 ttg aaa aac tgt tct ttc aat gta acc aca gaa aga aat aat aag aaa   384 aag aga gaa tac gcg ctt ttc tat aaa ctt gat gta gta cca att aac   432 gct aat aat aat agt act gca ggt gat tat atg cta ata aat tgt aat   480 gtt tca acc gtt aaa cag gct tgc cca aag gta acc ttt gag cca att   528 ccc ata cat tat tgt gct cca gct ggt tat gcg att cta aag tgt aat   576 gaa act aat ttc aat gga aca ggg cca tgc aaa aat gtc acc aca gta   624
```

-continued

```
caa tgc aca cat gga atc aag cca gta gta tca act caa cta ctg tta      672
aat ggc agt cta gca gaa gag aag ata atg att aga tct gaa aac ttc      720
aca gac aat act aaa aac ata ata gta cag ttt aac agt tct gta aga      768
att aat tgt acc aga cct aac aac aat aca aga aaa ggt ata cat ata      816
gga cca gga agg gct atc tat gca acg ggt gat ata ata ggg gat ata      864
aga caa gca cat tgt aat gtc agt aca gca gat tgg aat aac act tta      912
caa aag gta gct aag caa tta aga gag atc tac aac aaa aca ata atc      960
ttt act aaa cac tca gga ggg gat gta gaa att aca aca cat agc ttt     1008
aat tgt gga gga gaa ttt ttc tat tgc aat aca tca aga ttg ttt caa     1056
ggc aca tgg gac aag aaa aat gac act tgg aat tac cca ggg tca aat     1104
gac aat gac act ata act ctc cca tgc aga ata aag caa att gta cat     1152
atg tgg cag aga gta gga caa gca atg tat gcc cct ccc atc caa gga     1200
aaa ata gag tgt aaa tca aac att aca gga cta cta tta aca aga gat     1248
ggt ggg aat aaa aca caa aat gaa acc ttc aga cct aca gga gga gac     1296
atg agg gac aat tgg aga agt gaa tta tat aag tat aaa gta gtg gaa     1344
att aga cca cta gga gta gca ccc acc aag gca aaa aga aga gtg gtg     1392
cag                                                                 1395
```

SEQ ID NO:2, below is the amino acid sequence of CA1 gp120.

```
WVTVYYGVPV WRDADTTLFC ASDAKAYSTE KHNVWATHAC VPTDPDPQEI YLENVTENFN      60
MRKNNMVEQM HEDIISLWDE SLKPCVKLTP LCVTLNCTDV KTKNRTVEDQ AELKNCSFNV     120
TTERNNKKKR EYALFYKLDV VPINANNNST AGDYMLINCN VSTVKQACPK VTFEPIPIHY     180
CAPAGYAILK CNETNFNGTG PCKNVTTVQC THGIKPVVTST QLLLNGSLAE EKIMIRSENF    240
TDNTKNIIVQ FNSSVRINCT RPNNNTRKGI HIGPGRAIYA TGDIIGDIRQ AHCNVSTADW    300
NNTLQKVAKQ LREIYNKTII FTKHSGGDVE ITTHSFNCGG EFFYCNTSRL FQGTWDKKND    360
TWNYPGSNDN DTITLPCRIK QIVHMWQRVG QAMYAPPIQG KIECKSNITG LLLTRDGGNK    420
TQNETFRPTG GDMRDNWRSE LYKYKVVEIR PLGVAPTKAK RRVVQ                   465
```

The three variable loops (V1/V2, V3 and V4 are underscored and the Cys residues defining the beginning and end of each loop are bolded.

The three nucleic acid sequences encoding three consensus V3 loops of clade A1, and C are shown below.

SEQ ID NO:3 is a designed sequence that encodes the consensus V3 loop of clade A1:

```
TGC ACC CGC CCC AAC AAC AAC ACC CGC AAG AGC ATC CGC ATC GGC CCT       48
GGC CAG GCC TTC TAC GCC ACC GGC GAC ATC ATC GGC GAC ATC CGC CAG       96
GCC CAC TGC                                                          105
```

SEQ ID NO:4 is a designed sequence that encodes the consensus V3 loop of clade B:

```
TGT ACA AGA CCC AAC AAC AAT ACA AGA AAA AGT ATA CAC ATA GGA CCA    48
GGG AGA GCA TTC TAT ACA ACA GGA GAA ATA ATA GGA GAT ATA AGA CAA    96
GCA CAT TGT                                                       105
```

SEQ ID NO:5 is a designed sequence that encodes the consensus V3 loop of clade C:

```
TGT ACA AGA CCC AAC AAT AAT ACA AGA AAA AGT ATA AGG ATA GGA CCA    48
GGA CAA ACA TTC TAT GCA ACA GGA GAC ATA ATA GGA GAC ATA AGA CAA    96
GCA CAT TGT                                                       105
```

When the above consensus sequences are substituted into a codon optimized gp120 nucleic acid (SEQ ID NO:6) to replace the native V1/V2, V3 and V4 loops, the recombinant construct SEQ ID NO:6, below, results. This is a preferred DNA construct of the present invention that encodes "gp120/V3ABC". The three substituting sequences are underscored. The non-V loop parts of SEQ ID NO:6 differ from the wild type gp120-CA1 cDNA sequence (SEQ ID NO: 1). The A1, B and C V3 sequences (SEQ ID NO:3-5) are also not the wild type consensus sequence, as their codons were changed for optimal expression in mammalian cells. Of course the codon optimization does not change the amino acid sequences of the gp120-ABC protein.

```
                                                        (SEQ ID NO:6)
TGG GTG ACC GTG TAC TAC GGC GTG CCC GTG TGG AGA GAT GCC GAC AGC      48
ACC CTG TTC TGC GCC AGC GAC GCC AAG GCC TAC AGC ACC GAG AAG CAC      96
AAT GTG TGG GCC ACC CAC GCC TGC GTG CCC ACC GAC CCC GAC CCC CAG     144
GAG ATC TAC CTG GAG AAC GTG ACC GAG AAC TTC AAC ATG CGC AAG AAC     192
AAC ATG GTG GAG CAG ATG CAC GAG GAC ATC ATC AGC CTG TGG GAC GAG     240
AGC CTG AAG CCT TGC GTG AAG CTG ACC CCT CTG TGC GTG ACC CTG AAC     288
TGC ACC CGC CCC AAC AAC AAC ACC CGC AAG AGC ATC CGC ATC GGC CCT     336
GGC CAG GCC TTC TAC GCC ACC GGC GAC ATC ATC GGC GAC ATC CGC CAG     384
GCC CAC TGC AAC GTG AGC ACC GTG AAG CAG GCC TGC CCC AAA GTG ACC     432
TTC GAG CCC ATC CCC ATC CAC TAC TGC GCC CCT CGC GGC TAC GCC ATC     480
CTG AAG TGC AAC GAG ACC AAC TTC AAC GGC ACC GGC CCC TGC AAG AAT     528
GTG ACC ACC GTG CAG TGC ACC CAC GGC ATC AAG CCC GTG GTG AGC ACC     576
CAG CTG CTG CTG AAC GGC AGC CTG GCC GAG GAG AAG ATC ATG ATC CGG     624
AGC GAG AAT TTC ACC GAC AAC ACC AAG AAC ATC ATC GTG CAG TTC AAC     672
AGC AGC GTG CGC ATC AAT TGT ACA AGA CCC AAC AAC AAT ACA AGA AAA     720
AGT ATA CAC ATA GGA CCA GGG AGA GCA TTC TAT ACA ACA GGA GAA ATA     768
ATA GGA GAT ATA AGA CAA GCA CAT TGT AAT GTG TCT ACC GCC GAC TGG     816
AAC AAC ACC CTG CAG AAA GTG GCC AAG CAG CTG CGG GAG ATC TAC AAC     864
AAG ACC ATC ATC TTC ACC AAG CAC AGC GGC GGA GAT GTG GAG ATC ACC     912
ACC CAC AGC TTC AAT TGT GGC GGC GAG TTC TTC TAC TGT ACA AGA CCC     960
AAC AAT AAT ACA AGA AAA AGT ATA AGG ATA GGA CCA GGA CAA ACA TTC    1008
TAT GCA ACA GGA GAC ATA ATA GGA GAC ATA AGA CAA GCA CAT TGT CGG    1056
ATC AAG CAG ATC GTG CAC ATG TGG CAG CGC GTG GGC CAG GCC ATG TAC    1104
GCC CCT CCC ATC CAG GGC AAG ATC GAG TGC AAG AGC AAC ATC ACC GGC    1152
```

-continued

```
CTG CTG CTG ACC AGA GAT GGC GGC AAC AAG ACC CAG AAC GAG ACC TTC     1200

AGA CCC ACA GGC GGC GAC ATG AGG GAC AAC TGG CGG AGC GAG CTG TAC     1248

AAG TAC AAA GTG GTG GAG ATC AGA CCC CTG GGC GTG GCC CCC ACC AAG     1296

GCC AAG AGA AGA GTG GTG CAG                                         1317
```

This above nucleic acid molecule is a preferred DNA immunogen for priming a more potent anti V3 immune response, in particular, a stronger and more broadly reactive antibody response.

SEQ ID NO:7, below, adds a 5' and a 3' restriction enzyme site (cloning sites) as well as a stop codon ("TGA") to SEQ ID NO:6; these sites are underscored:

```
GGT ACC GCT AGC TGG GTG ACC GTG TAC TAC GGC GTG CCC GTG TGG AGA    48
GAT GCC GAC ACC ACC CTG TTC TGC GCC AGC GAC GCC AAG GCC TAC AGC    96
ACC GAG AAG CAC AAT GTG TGG GCC ACC CAC GCC TGC GTG CCC ACC GAC   144
CCC GAC CCC CAG GAG ATC TAC CTG GAG AAC GTG ACC GAG AAC TTC AAC   192
ATG CGC AAG AAC AAC ATG GTG GAG CAG ATG CAC GAG GAC ATC ATC AGC   240
CTG TGG GAC GAG AGC CTG AAG CCT TGC GTG AAG CTG ACC CCT CTG TGC   288
GTG ACC CTG AAC TGC ACC CGC CCC AAC AAC AAC ACC CGC AAG AGC ATC   336
CGC ATC GGC CCT GGC CAG GCC TTC TAC GCC ACC GGC GAC ATC ATC GGC   384
GAC ATC CGC CAG GCC CAC TGC AAC GTG AGC ACC GTG AAG CAG GCC TGC   432
CCC AAA GTG ACC TTC GAG CCC ATC CCC ATC CAC TAC TGC GCC CCT GCC   480
GGC TAC GCC ATC CTG AAG TGC AAC GAG ACC AAC TTC AAC GGC ACC GGC   528
CCC TGC AAG AAT GTG ACC ACC GTG CAG TGC ACC CAC GGC ATC AAG CCC   576
GTG GTG AGC ACC CAG CTG CTG CTG AAC GGC AGC CTG GCC GAG GAG AAG   624
ATC ATG ATC CGG AGC GAG AAT TTC ACC GAC AAC ACC AAG AAC ATC ATC   672
GTG CAG TTC AAC AGC AGC GTG CGC ATC AAT TGT ACA AGA CCC AAC AAC   720
AAT ACA AGA AAA AGT ATA CAC ATA GGA CCA GGG AGA GCA TTC TAT ACA   768
ACA GGA GAA ATA ATA GGA GAT ATA AGA CAA GCA CAT TGT AAT GTG TCT   816
ACC GCC GAC TGG AAC AAC ACC CTG CAG AAA GTG GCC AAG CAG CTG CGG   864
GAG ATC TAC AAC AAG ACC ATC ATC TTC ACC AAG CAC AGC GGC GGA GAT   912
GTG GAG ATC ACC ACC CAC AGC TTC AAT TGT GGC GGC GAG TTC TTC TAC   960
TGT ACA AGA CCC AAC AAT AAT ACA AGA AAA AGT ATA AGG ATA GGA CCA  1008
GGA CAA ACA TTC TAT GCA ACA GGA GAC ATA ATA GGA GAC ATA AGA CAA  1056
GCA CAT TGT CGG ATC AAG CAG ATC GTG CAC ATG TGG CAG CGC GTG GGC  1104
CAG GCC ATG TAC GCC CCT CCC ATC CAG GGC AAG ATC GAG TGC AAG AGC  1152
AAC ATC ACC GGC CTG CTG CTG ACC AGA GAT GGC GGC AAC AAG ACC CAG  1200
AAC GAG ACC TTC AGA CCC ACA GGC GGC GAC ATG AGG GAC AAC TGG CGG  1248
AGC GAG CTG TAC AAG TAC AAA GTG GTG GAG ATC AGA CCC CTG GGC GTG  1296
GCC GCC ACC AAG GCC AAG AGA AGA GTG GTG CAG TGA GGA TCC GAG CTC  1344
```

SEQ ID NO:8 is the amino acid sequence encoded by the preferred DNA constructs above (SEQ ID NO:6) and represents the "gp120-ABC" polypeptide of the present invention.

sequences of CA1. Also shown is the amino acid sequence (gp120-ABC-r; SEQ ID NO:9) which include residues corresponding to added N- and C-terminal amplifications sites

```
WVTVYYGVPV  WRDADTTLFC  ASDAKAYSTE  KHNVWATHAC  VPTDPDPQEI  YLENVTENFN   60

MRKNNMVEQM  HEDIISLWDE  SLKPCVKLTP  LCVTLNCTRP  NNNTRKSIRI  GPGQAFYATG  120

DIIGDIRQAH  CNVSTVKQAC  PKVTFEPIPI  HYCAPAGYAI  LKCNETNFNG  TGPCKNVTTV  180

QCTHGIKPVV  STQLLLNGSL  AEEKIMIRSE  NFTDNTKNII  VQFNSSVRIN  CTRPNNNTRK  240

SIHIGPGRAF  YTTGEIIGDI  RQAHCNVSTA  DWNNTLQKVA  KQLREIYNKT  IIFTKHSGGD  300

VEITTHSFNC  GGEFFYCTRP  NNNTRKSIRI  GPGQTFYATG  DIIGDIRQAH  CRIKQIVHMW  360

QRVGQAMYAP  PIQGKIECKS  NITGLLLTRD  GGNKTQNETF  RPTGGDMRDN  WRSELYKYKV  420

VEIRPLGVAP  TKAKRRVVQ.                                                  439
```

SEQ ID NO:9, below, is the amino acid sequence encoded by the DNA construct SEQ ID NO:7, and is the same as SEQ ID NO:8, with the addition of four residues at both termini encoded by the cloning sites (shown as italic, double underscore, nonbolded).

(plus the site of the stop codon). The replacement order of the V3 regions is as follows: native V1/V2 is replaced by V3-A1 (consensus V3 of clade A1). The native V3 region is replaced by V3-B (consensus V3 of Clade B). The native V4 region is replaced by V3C (the consensus V3 of clade C).

```
GTASWVTVYY  GVPVWRDADT  TLFCASDAKA  YSTEKHNVWA  THACVPTDPD  PQEIYLENVT   60

ENFNMRKNNM  VEQMHEDIIS  LWDESLKPCV  KLTPLCVTLN  CTRPNNNTRK  SIRIGPGQAF  120

YATGDIIGDI  RQAHCNVSTV  KQACPKVTFE  PIPIHYCAPA  GYAILKCNET  NFNGTGPCKN  180

VTTVQCTHGI  KPVVSTQLLL  NGSLAEEKIM  IRSENFTDNT  KNIIVQFNSS  VRINCTRPNN  240

NTRKSIHIGP  GRAFYTTGEI  IGDIRQAHCN  VSTADWNNTL  QKVAKQLREI  YNKTIIFTKH  300

SGGDVEITTH  SFNCGGEFFY  CTRPNNNTRK  SIRIGPGQTF  YATGDIIGDI  RQAHCRIKQI  360

VHMWQRVGQA  MYAPPIQGKI  ECKSNITGLL  LTRDGGNKTQ  NETFRPTGGD  MRDNWRSELY  420

KYKVVEIRPL  GVAPTKAKRR  VVQGSEL                                         447
```

In the foregoing sequence, bold underscored font represents the consensus V3 sequence of clade A1 replacing the V1/V2 loop of HIV-1 CA1. The italicized font shows the consensus V3 sequence of clade B replacing the V3 loop of CA1. The bold, double underscored font shows the consensus V3 sequence of clade C replacing the V4 loop of CA1.

Table 1, below, shows alignments of the sequence of gp120 from the clade A strain CA1 (gp120-CA1; SEQ ID NO:2)) which is an example of a "source" strain exemplified herein and the sequence of the recombinant sequence of the present invention, "gp120-V3-ABC" is a modified CA1 sequence (SEQ ID NO:8) in which three V3 sequences (designated A, B and C) are substituted for the native V1/V2, V3 and V4, The "gp120-ABC" DNA vaccine can express functional gp120 protein with 3 V3 regions. The "gp120-ABC" protein expressed in transiently transfected 293T cells (human embryonic kidney cell line) can be recognized by gp120 specific rabbit serum (FIG. 1).

Additional examples of V3 sequences that may be used in the recombinant immunogenic DNA molecules of the present invention include those listed in Tables 2 and 3—which are "organized" according to the different co-receptor tropisms of HIV-1.

In addition to natural viral V3 loop sequences or consensus sequences thereof, the constructs of the present invention may comprise nucleotide sequences that encode amino acid sequences that are not found in viral isolates in nature. They may be sequences discovered, for example, through structural studies (e.g. X ray crystallographic or NMR studies) and may be sequences that prove to be better able to induce even broader and more potent immune responses against the HIV-1 envelope. Several examples of such sequences or epitopes are described in WO2004/069863 (Anglister et al., co-invented present inventor Zolla-Pazner) which document is incorporated by reference in its entirety.

Table 4 sets out DNA and protein antigens, and a program of administration of DNA and protein antigens to rabbits to achieve the desired anti-V3 antibody responses. It should be evident that, while clade A1, B and C are listed, it is possible to substitute a consensus sequence (or an individual sequence) of any clade in the chimeric gp120 DNA molecule of the present invention. used for priming (or immunization).

Moreover, a similar protocol is used to prime and boost humans to make more potent and broader anti-V3 antibody responses.

TABLE 1

Amino acid sequence alignment of original gp120-CA1 and produced gp 120-V3-ABC

```
gp120-CA1       1  ----WVTVYYGVPVWRDADTTLFCASDAKAYSTEKHNVWATHACVPTDPDPQEIYLENVT  60
gp120-V3-ABC    1  ----........................................................
gp120-V3-ABC-r  1  GTAS........................................................

V1/V2
gp120-CA1      61  ENFNMRKNNMVEQMHEDIISLWDESLKPCVKLTPLCVTLNCTDVKTKNRTVEDQAELKNC 120
gp120-V3-ABC       ........................................[..RPNNNTRKSIRIGPQAF
gp120-V3-ABC-r     ........................................[..RPNNNTRKSIRIGPQAF
                                                                   Cons-V3-A1 gp120-CA1     121  SFNVTTERNNKKKREYALFYKLDVVPINANNNSTAGDYMLINCNVSTVKQACPKVTFEPI 180
gp120-V3-ABC       YATGDIIGDIRQAHC]--------------------------------.............
gp120-V3-ABC-r     YATGDIIGDIRQAHC]--------------------------------.............

gp120-CA1     181  PIHYCAPAGYAILKCNETNFNGTGPCKNVTTVQCTHGIKPVVSTQLLLNGSLAEEKIMIR 240
gp120-V3-ABC       ............................................................
gp120-V3-ABC-2     ............................................................

V3
gp120-CA1     241  SENFTDNTKNIIVQFNSSVRINCTRPNNNTRKGIHIGPGRAIYATGDIIGDIRQAHCNVS 300
gp120-V3-ABC       .....................[..........S........F.T..E..........]...
gp120-V3-ABC-r     .....................[..........S........F.T..E..........]...
                                         Cons-V3-B gp120-CA1     301  TADWNNTLQKVAKQLREIYNKTIIFTKHSGGDVEITTHSFNCGGEFFYCN--TSRLFQGT 360
gp120-V3-ABC       ...........................................[.TRPNNNTRKSI
gp120-V3-ABC-r     ...........................................[.TRPNNNTRKSI V4
gp120-CA1     361  WDKKNDTWNYPGSNDNDTITLPCRIKQIVHMWQRVGQAMYAPPIQGKIECKSNITGLLLT 420
gp120-V3-ABC       RIGPGQ.FYAT.DIIG.IRQAH.]....................................
gp120-V3-ABC-r     RIGPGQ.FYAT.DIIG.IRQAH.]....................................
                     Cons-V3-B gp120-CA1     421  RDGGNKTQNETFRPTGGDMRDNWRSELYKYKVVEIRPLGVAPTKAKRRVVQ-----      476
gp120-V3-ABC       ..................................................-----
gp120-V3-ABC-r     .................................................*GSEL
``` gp120-CA1:
original amino sequence of gp120-CA1 of clade A. The italic underlined sequences are V1/V1, V3 and V4 regions respectively as indicated in the original gp120-CA1 sequence. (SEQ ID NO:2
gp120-V3-ABC:
gp120-CA1 amino acid sequence in which V3 A, B and C are substituted for V1/V2, V3 and V4, respectively. (SEQ ID NO:8
gp120-V3-ABC-r:
amino acid sequence (SEQ ID NO:9) encoded by SEQ ID NO:7) produced (same as gp120-V3-ABC). SEQ ID NO:9 The four extra amino acids at both termini are translation products of added restriction sites that permit amplification of the DNA in expression plasmids.
Cons-V3-A1, Cons-V3-B and Cons-V3C:
V3 consensus sequences of clades A1, B and C, respectively, as shown in the boxes.
"." indicates identity to gp120-CA1 of clade A at that position.
"-" indicate absence of amino acid residues at those positions.
"*" indicates the end of protein by stop codon in the DNA sequence.

TABLE 2

Consensus and Individual V3 Sequences of R5-tropic HIV-1 Strains

| | | | SEQ ID NO: |
|---|---|---|---|
| R5 | Consensus | CtRPdNNTR+t#.IGPG.%#YATGdIIGdIRqA#C | 10 |
| D1P95 | (7) | CTRPNNNTRKSINIAPGRAFYATGDIIGDIRQAHC | 11 |
| LP1296 | (5) | CTRPNNNTRKSIHIQPGRAFYATGEIIGDIRQAHC | 12 |
| W2P96 | (7) | CTRPNNNTRKSIHIGPGRAFYATGDIIGDIRQAHC | 13 |
| W60C | (7) | CTRPNNNTRKSIHIGPGRAFYTTGDIIGDIRQAHC | 14 |
| W69P | (6) | CIRPNNNTRKSIHMGPGRAFYATGDIIGNIRQAHC | 15 |
| CMNYU5487 | (5) | CVRPNNNTRKSIHIGPGQAFYATGDIIGNIRQAHC | 16 |
| CMNYU1423 | (5) | CTRPNNNTRKSIHIGPGQAFYATGDIIGNIRQAHC | 17 |
| CMNYU360 | (6) | CTRPNNNTRKSVHIGPGRAFYGIGDIIGNIRQAHC | 18 |
| CMNYU2395 | (4) | CTRPNNNTRKGVHIGPGRTFYATGEIIGNIRQAHC | 19 |
| CMNYU809 | (6) | CTRPNNNTRKGIHIGPGRTFYATDAIIGNIRQAHC | 20 |
| W64C | (6) | CTRPNNNTRKGINMGPGRAFYATTDIVGDIIQAHC | 21 |
| CMNYU5821 | (6) | CTRPNNNTRTGVHIGPGRAFYATGDIIGDIRQAHC | 22 |
| CMNYU6283 | (7) | CIRPNNNTRKSIRIGPGQAFYARGDVISNIRHAYC | 23 |
| CMNYU358 | (6) | CIRPNNNTRKSIHIGPGQAFYARGDIIGNIRQAYC | 24 |
| CMNYU1545 | (5) | CVRPNNNTRRSIHIGPGQALYATGRIIGNIRQAYC | 25 |
| CMNYU5184 | (8) | CIRGNNNTRKSMRIGPGQAFYATGDIIGDIRRAYC | 26 |
| CMNYU4730 | (6) | CIRGNNNTRKSVRIGPGQTFYTHGAIIGDIRQAHC | 27 |
| CMNYU1989 | (6) | CTRPGNNTRRSISIGPGQAFYTT-DIIGDIRQAYC | 28 |
| CMNYU2845 | (8) | CIRPNNNTRKSIPIGPGRAFYATGDIIGDIRKAYC | 29 |
| CMNYU1500 | (7) | CSRPNNNTRKSIHIGPGRAFYATDDIIGNIRQAYC | 30 |
| CMNYU1678 | (6) | CTRPGNNTRKSIRIGPGQTFYATGDIIGNIRQAHC | 31 |
| CMNYU5203 | (7) | CTRPGNNTRKSVRIGPGQTFYATGDIIGDIRQAHC | 32 |
| CMNYU5285 | (6) | CTRPGSNTRKSIRIGPGQAFYATGDVIGDIREASC | 33 |
| CMNYU1532 | (3) | CTRPGNNTRKSIRIGPGQVLYATGEIIGEIRQAYC | 34 |
| CMNYU5855 | (5) | CTRPNNNTRKSVRIGPGQTFYATGDIIGEIRQAYC | 35 |
| CMNYU4717 | (5) | CTRPNNNTRESVRIGPGQTFYATGDIIGDIRQAHC | 36 |
| CMNYU1261 | (5) | CTRPNNNTRRSIGIGPGQTIYATGAIIGDIRQAHC | 37 |
| CMNYU5466 | (5) | CTRPSNNTRKGWHIGPGQTLYATGAIIGDIRQAHC | 38 |
| CMNYU5346 | (5) | CTRPNNNTRKSIRIGPGQALYATGAIIGNIRQAHC | 39 |
| CMNYU2541 | (6) | CTRPNNNTRKSIGIGPGQVFYATGDIIGDIRQAHC | 40 |
| CMNYU786 | (5) | CTRPGNNTRKGIGIGPGQMFYATGSIIGDIRQAHC | 41 |
| W67P | (7) | CTRPNNNTRRSIPMGPGKAFYATGDIIGDIRQAHC | 42 |
| CMNYU5308 | (5) | CTRPSNNTRKSIPIGPGQAIYATGEIIGDIRKAHC | 43 |
| CMNYU5887 | (7) | CTRPNNNTRKSIHMGPGQAMYVTGDIIGDIRRAHC | 44 |
| tz19 | (4) | CTRPNNNTRESIRIGPGQTFYATGDIIGDIRQAHC | 45 |
| tz14 | (5) | CTRPNNNTRKSIRIGPGQTFYATGDIIGDIRQAHC | 46 |

TABLE 2-continued

| Consensus and Individual V3 Sequences of R5-tropic HIV-1 Strains | | | SEQ ID NO: |
|---|---|---|---|
| tz5 | (5) | CTRPNNNTRKSIRIGPGQVFYATGDIIGDIRQAHC | 47 |
| tz13 | (5) | CIRPNNNTRKSVRIGPGQAFYATGDIIGDIRQAHC | 48 |
| tz9 | (5) | CVRPSNNTRKSIRIGPGQTFYATGDITGDIRQAHC | 49 |
| tz21 | (4) | CTRPSNNTRQGIHIGPGQALYTT-KIIGDIRQAHC | 50 |
| tz7 | (4) | CTRPNNNTRKSIHIGPGQAFYAIGDVIGNIRQAQC | 51 |
| tz11 | (4) | CIRPNNNTRKSVHIGPGQTFYATGDIIGNIRQAHC | 52 |

TABLE 3

Consensus and Individual V3 Sequences of X4 tropic HIV-1 Strains

| Position | | | SEQ ID NO: |
|---|---|---|---|
| X4 | Cons | CTRPNNNtR.+RI.#GPGRA#Y.TG.I#.GdI+.A#C | 53 |
| DY1C | (6) | CTRPNNNTR-KRIHIGPGRAFYTTGQII--GNIRQAYC | 54 |
| 71_1C1 | (6) | CTRPNNNTR-KRIHIGPGRAFYTTGQII--GNIRQAHC | 55 |
| 72_C9 | (7) | CTRPNNNTR-KRIHIGPGRAFHTTGAII--GKIRQAHC | 56 |
| RRmtc_ | (6) | CTRPNNNTR-KRIHIGPGRAFYTTGGII--GNIRQAHC | 57 |
| DY11P_ | (8) | CTRPNNNTR-KRIHIGPGRAFYATGKII--GDIRQAHC | 58 |
| 12P49_ | (7) | CIRPNNNTR-RRIHIGPGRAFYATGRII--GNIRQAYC | 59 |
| W12P04 | (8) | CIRPNNNTR-RSIHIGPGRAFYATGRII--GDIRRAYC | 60 |
| AF2P12 | (6) | CIRPNNNTR-TKIRIGPGQAFYATGNII----GDIRQAYC | 61 |
| DY9P_7 | (6) | CLRPNNNTR-KRIHLGPGRAFYAAGEII--GKIRQAHC | 62 |
| P1T6C | (9) | CTRPNNNIR-RRIHIGPGRAFYATGDII--GDIRKAYC | 63 |
| P1T36C | (9) | CTRPNNNTR-RRIHIGPGRAFYATGDTI--GDIRKAYC | 64 |
| AF10P9 | (9) | CTRPNDNIR-KRVHIGPGQAFYATGDVI--GDIRRAHC | 65 |
| P14T0C | (9) | CTRPNNNIR-RRIHIGPGRAFYATGGIR--GDIRKAYC | 66 |
| Acmtc | (9) | CTRPNNNIR-RRIRIGPGRAYFTRGQIK--EHMRKAHC | 67 |
| CMmtc | (10 | CTRPSNNTR-KRIPIGPRRAFYATGDIV--GDIRRAHC | 68 |
| P5T0C | (7) | CTRPNNHTR-KRMTLGPGRVYYTTGEIL--GDIKKAHC | 69 |
| P5T6C | (7) | CTRPNNHTR-KRMTLGPGKVYYTTGEIV----GDIKKAHC | 70 |
| XP6_6 | (6) | CTRPNNHTR-KRISLGPGRAYYTTGEIV--GSIKKAHC | 71 |
| WP4_14 | (9) | CTRPNNNTR-KRIRIGPGRAVYTTGKII--GKIRQAHC | 72 |
| FR3_4 | (9) | CTRPNTNKR-KRTTKGPGRVIYATGQII--GKIRQAHC | 73 |
| VE15_2 | (6) | CTRPNNNTR-KRISIGPGRAFYTTGQII--GNIRQAHC | 74 |
| DE2_4 | (6) | CTRPNNNTR-KRISIGPGRAFYTIGQII--GNIRQAHC | 75 |
| W17P07 | (6) | CTRPNNNTR-KGISVGPGRAIYATKNII--GDISQAHC | 76 |
| W2P069 | (6) | CTRPKNNTR-KPIHIGPGRAFYATREIR--GNIIQAHC | 77 |
| 17P7_9 | (6) | CTRPNNNTR-KRISVGPGRAFYATGNII--GKISQAHC | 78 |

TABLE 3-continued

Consensus and Individual V3 Sequences of X4 tropic HIV-1 Strains

| Position | | | SEQ ID NO: |
|---|---|---|---|
| EV5_2 | (8) | CTRPNNNTR-KRIRIGPGRAFYTTGQII---GDIRQAHC | 79 |
| AF9P2 | (4) | CTRPNNNTI-TRIRIGPGQAFYATGSII--GNIRQAHC | 80 |
| tz23 | (8) | CSRPYKKER-QRTHIGPGQALYTTRTTRVEGNIRQAHC | 81 |
| tz4 | (7) | CVRPYRNIKIQRTPIGLGQALYTTKRI---GHIGQAHC | 82 |

TABLE 4

| | Priming | gp120-ABC DNA priming (2X)* | | Protein boost (2X)** | |
|---|---|---|---|---|---|
| Group # | Immunogen | gp120 DNA | Dose (μg) | V3-fusion protein (fp) | Doses (μg)( |
| 100 | Monovalent | Clade A1 | 36 | A1 + B + C fp's | 100 each |
| 101 | | Clade B | | | |
| 102 | | Clade C | | | |
| 201 | Mixture | clade A1 gp120 + clade B gp120 + clade C gp120 | 36 (12 each) | A1-FP | 100 |
| 202 | Mixture | clade A1 gp120 + clade B gp120 + clade C gp120 | | B-FP | 100 |
| 203 | Mixture | clade A1 gp120 + clade B gp120 + clade C gp120 | | C-FP | 100 |
| 204 | Mixture | clade A1 gp120 + clade B gp120 + clade C gp120 | | A1 + B + C fp's | 100 (33.3 each) |
| 301 | 3-valent | "gp120-ABC" | 36 | A1-FP | 100 |
| 302 | | "gp120-ABC" | | B-FP | 100 |
| 303 | | "gp120-ABC" | | C-FP | 100 |
| 304 | | "gp120-ABC" | | A1 + B + C fp's | 100 (33.3 each) |
| C01 | Control | None (Vector control) | 36 | A1-FP | 100 |
| C02 | | None (Vector control) | | B-FP | 100 |
| C03 | | None (Vector control) | | C-FP | 100 |
| C04 | | None (Vector control) | | V3/A1 + V3/B + V3/C | 100 (33.3 each) |

*DNA priming at days 0 and 14 days.
**Protein boosting at days 42 and 70

Antisera from subjects immunized as above—initially experimental animals, preferably rabbits, are assayed for levels of and clade breadth of anti-V3 antibodies using conventional ELISA and neutralization assays as described below (and in numerous publications such as Gorny M K et al., 2004, *Virology* 78:2394-2404; Gorny M K et al., 2002, *J. Virol.* 76:9035-45 (and the references cited therein). Other conventional immunoassay formats may be used to study these antibody responses.

The immunogenic composition of this invention may further comprise one or more adjuvants or immunostimulating agents—which are preferably added to the polypeptide immunogens using for boosting the immune response. An adjuvant is any substance that can be added to an immunogen or to a vaccine formulation to enhance the immune-stimulating properties of the immunogenic moiety, such as a protein or polypeptide. Liposomes are also considered to be adjuvants. See, for example, Gregoriades, G. et al., *Immunological Adjuvants and Vaccines*, Plenum Press, New York, 1989; Michalek, S. M. et al., Liposomes as Oral Adjuvants, *Curr. Top. Microbiol. Immunol.* 146:51-58 (1989). Examples of adjuvants or agents that may add to the effectiveness of V3 DNA or peptides as immunogens include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g. N-acetyl-D-glucosaminyl-(β1-4)-N-acetylmuramyl-L-alanyl-D-isoglutamine (GMDP) (Hornung, R L et al., *Ther Immunol* 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al., (1992) *N. Engl. J. Med.,* 327: 1209-1238) and monophosphoryl lipid A adjuvant solubilized in 0.02% triethanolamine. Other useful adjuvants are, or are based on, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives [such as QS21 (White, A. C. et al. (1991) *Adv. Exp. Med. Biol.,* 303:207-210) which is now in use in the clinic (Helling, F et al. (1995) *Cancer Res.,* 55:2783-2788; Davis, T A et al. (1997) *Blood,* 90: 509A (abstr.)], levamisole, DEAE-dextran, blocked copolymers or other synthetic adjuvants. Examples of commercially available adjuvants include (a) Amphigen®, an oil-in-water adjuvant made of de-oiled lecithin dissolved in an oil (see for example, U.S. Pat. No. 5,084,269 and US Pat Publication 20050058667A1 and (b) Alhydrogel® which is an aluminum hydroxide gel. Aluminum is approved for human use. Adjuvants are available commercially from various sources, for example, Merck Adjuvant 65® (Merck and Company, Inc., Rahway, N.J.). The immunogenic material may be adsorbed to or conjugated to beads such as latex or gold beads, ISCOMs, and the like.

The immunogenic composition may also be supplemented with an immunostimulatory cytokine, lymphokine or chemokine. Preferred cytokines are GM-CSF (granulocyte-macrophage colony stimulating factor), interleukin 1, interleukin 2, interleukin 12, interleukin 18 or interferon-γ.

General methods to prepare immunogenic pharmaceutical compositions and vaccines are described in Remington's Pharmaceutical Science; Mack Publishing Company Easton, Pa. (latest edition).

Having now generally described the invention, the same will be more readily understood through reference to the following examples which are provided by way of illustration, and are not intended to be limiting of the present invention, unless specified.

EXAMPLE I

Methods

DNA Immunization

Female New Zealand rabbits (2 kg) receives three monthly DNA immunizations by gene gun. Each shot delivers 1 µg of DNA and a total of 36 non-overlapping shots are delivered to each rabbit at each of the three time points at the surface of shaved abdominal skin after animals are anesthetized according to IACUC approved protocols. The serum samples are collected immediately before, and 2 weeks after each immunization.

ELISA (Enzyme-Linked Immunosorbent Assay).

Rabbit serum samples are tested for gp120-specific and for V3 peptide-specific IgG antibody responses by ELISA. Microplates are coated with ConA (5 µg/well) for 1 hour and then washed 5 times with washing buffer (PBS at pH 7.2 with 0.1% Triton X-100). gp120 at 1 µg/ml is added (100 µl for each well) and incubated for 1 hour at room temperature. Alternatively, V3 peptides or other recombinant proteins containing V3 sequences are coated directly onto microplates (see Gorny et al., 2002, 2004, supra). For blocking, 200 µl/well of 4% milk-whey blocking buffer was incubated for 1 hour at room temperature. After removal and another 5 washes, 100 µl of serially diluted sera are added and incubated for 1 hour. The plates are washed 5 times and incubated with 100 µl of biotinylated anti-rabbit IgG diluted at 1:1000 for 1 hour followed by washes.

Horseradish peroxidase-conjugated streptavidin diluted at 1:2000 is added (100 µl/well) and incubated for 1 hour. After the final washes, 100 µl/well of fresh TMB substrate is added and allowed to incubate for 3.5 min. The reaction is stopped by adding 25 µl of 2M $H_2SO_4$, and the absorbance (optical density=OD) of the colored product in each well is measured at 450 nm (also referred to as $A_{450}$).

Assays in which serum reactivity to gp120 is evaluated are described in examples below. Table 5 shows results of these assays.

Western Blot Analysis

The gp120 antigens transiently expressed from 293T-cell supernatants and cell lysates are subjected to denaturing SDS-PAGE and blotted onto polyvinylidene fluoride (PVDF) membrane. Blocking is done with 0.1% I-Block. Rabbit immune serum with mixed polyvalent gp120 DNA vaccines is used as the detecting antibody at 1:500 dilution and incubated for 45 minutes. Subsequently, the membranes are washed with blocking buffer and then reacted with alkaline phosphatase (AP)-conjugated goat anti-rabbit or human IgG at 1:5000 dilution. After final wash, Western-Light® substrate is applied to the membranes for 5 minutes. Once the membranes are dry, Kodak film is exposed to the membrane and developed with an X-Omat processor. Env reactivity is also observed by Western blot.

Neutralization Assays

One way of determining the potential efficacy of a vaccine in animals is to perform in vitro functional assays of the animal's immune sera. The peripheral blood mononuclear cell (PBMC) assay and the MT-2 assay are two of several assays commonly used for evaluating antibody responses in vaccinated test animals in vitro.

MT-2 Syncytia Inhibition Assay

MT-2 is a T cell line that is induced to form syncytia by HIV-1$_{IIIB}$ and HIV-1$_{MN}$ (a B-clade laboratory strain). Inhibition of syncytia formation serves as a measure of HIV-1 neutralizing antibodies (Montefiori et al., 1988, J. Clin. Microbiol. 26:231-237). The inhibition of syncytia formation by a test antiserum is a reflection of neutralizing antibodies present in the serum that have been induced by vaccination. Briefly, vaccinated test and control sera are incubated with an HIV-1 infected culture of MT-2 cells in microplates. In control wells (no neutralizing antibodies, HIV-1 causes cytopathic effects in about >70% but less than 100% of the cells). Viable cells are stained with Finter's neutral red stain. Neutralization is assessed as a reduction in cell death (increase in stained viable cells). The Percentage protection is determined by calculating the difference in absorption ($A_{540}$) of test wells (cells+virus) and dividing this result by the difference in absorption between control wells (cells only) and virus control wells (virus only). Neutralizing titers are expressed as the reciprocal of the dilution of the test serum or plasma required to protect at least 50% of cells from virus-induced killing.

PBMC Assay

The presence of neutralizing antibodies in the serum of a vaccinated animal can also be tested in a functional assay referred to as a neutralization assay. Rabbits are immunized as described above with a monovalent vaccine or "polyvalent" vaccine. The immune sera are applied to peripheral blood mononuclear cells (PBMCs) infected with different primary viral isolates. Results from this assay are expressed as percent inhibition of virus as compared with the virus control without immunized rabbit sera. Results from the monovalent vaccinations show a general trend towards the ability to autologously respond.

Cell-Mediated Immune Assays

Cell-mediated immune responses can also be tested to evaluate the functional capacities of immune cells of vaccinated animals. For determining the potential efficacy of a vaccine in humans, these in vitro assays can also be performed with lymphocytes isolated from human subjects. (see, for example, Cristillo, A D et al., 2006, Virology 346:151-68 (Epub 2005, Dec. 2).

EXAMPLE II

DNA Vaccination and Protein Boosting Rabbits

DNA and protein compositions are prepared with V3 sequences shown in Table 1. The antigens are administered to rabbits according to the design presented in Table 4. Briefly, rabbits are immunized with monovalent gp120 with a single V3 loop (monovalent prime), with a mixture of DNA coding for three different gp120s (mixture prime), or trivalent recombinant gp120, i.e., gp120-ABC (trivalent prime), or control DNA vaccines at 0 and 14 days, as indicated. Animals receive protein boosts at week days 42 and 70. Neutralization of primary HIV-1 isolates by sera from immunized animals is measured.

Results are as follows:

A. Control groups C01-C04 receiving no priming develop low titers of neutralizing Abs (<1:40) and display some, but minimal, cross-clade neutralizing antibody activity.

B. Groups 100-102 receiving monovalent priming and monovalent boosting develop somewhat higher titers of neutralizing Abs (1:40-1:160) and display some, but minimal, cross-clade neutralizing antibody activity.

C. Groups 201-203 primed with a mixture of gp120's priming and monovalent priming will have relatively lower titers of neutralizing antibody activity (1:40-1:80), due to a "dilution" in the doses of individual priming and individual boosting antigens they encounter. Their antibodies will show some, albeit minimal cross-clade neutralizing activity. Group 204, that is primed with a mixture of gp120 DNAs and is boosted with a mixture of V3 fusion proteins will have the same level of Abs (due to reduced exposure to each antigen) but with a greater breadth of cross-clade neutralizing Abs D. Groups 301-303 primed with trivalent recombinant gp120-ABC and monovalent boosts will have higher levels of neutralizing Abs due to better memory (>1:160) with limited breadth, whereas Group 304 that receives the trivalent recombinant gp120-ABC and the mixed boost with three V3 fusion proteins will have the highest neutralizing titers (>1:320) with the greatest breadth of neutralizing activity.

Significant neutralizing antibody responses (titers of ~10-300) are found at the end of DNA priming compared to animals receiving empty DNA vectors, where there is no detectable neutralizing antibody (Wang, S et al., supra).

It is concluded that DNA immunization alone is not sufficient to induce strong neutralizing antibody responses but that DNA priming is very useful for subsequent rapid induction of broadly neutralizing antibody responses after 1 or 2 boosts with the corresponding protein antigens, and that such antibodies are reactive against primary HIV-1 isolates that are often difficult to neutralize.

EXAMPLE II

Assaying Protective Immunity

The efficacy of any DNA vaccine of the present invention can be tested in an appropriate animal model. Preferably, responses in animals that can be infected by HIV are tested, such as a non-human primate (e.g., a chimpanzee) or an animal such as a mouse which has circulating human immune cells. Large enough numbers of animals are be used to achieve statistical significance, though in the case of non-human primates, the numbers may be limited and thus the experiments may be need to be repeated in the same animal, for example. Once the test animals are vaccinated and control animals are vaccinated with a negative control containing the same vector, but without the heterologous gp120 DNA, both groups of animals are then infected with HIV-1. They may be infected with primary isolates or with laboratory strains, or both (or SHIV, in the case of macaque experiments). After a suitable amount of time, at which the animals vaccinated with a negative control vaccine begin to show a decline in T cell number and/or the presence of plasma virus, the presence of a protective immune response can be compared in test and control animals.

One way to test a protective immune response is to obtain sera from the animals and use an ELISA as above to test for the presence or titer of specific IgG antibody.

The animals can also be monitored for the absence or presence (and time of onset or detection) of the infection relative to negative controls using known methods.

The efficacy of a vaccine can be evaluated in uninfected animals by performing in vitro functional assays of immune cells. Neutralizing antibody from vaccinated animals can be assayed as above (e.g., mice, rats, rabbits, non-human primates), which have not been infected with HIV.

Cell-mediated immune responses (e.g., CTL responses) can be tested in animals without infecting them. Lymphocytes can be obtained and isolated from peripheral blood or from organized lymphatic tissues, such a lymph nodes or spleens. The cells are then exposed to a conventional V3 peptide antigen which can stimulate primed T cells in vitro to express their CTL activity.

ELISPOT and/or Intracellular Cytokine Staining (ICS) may also performed to enumerate the T cells producing and/or releasing a given cytokine.

Known infectivity assays that measure resistance of cells to HIV infection can be performed.

The best test of protection is to challenge the animals with HIV-1. However there is no definitive and reproducible way to infect a non-human animal with HIV. SHIV infection of non-human primates has been tested. The current standard for testing animals for responses to vaccination is, as noted, (1) isolation of immune cells functional tests for activity against the antigen against which they are putatively immunized, in this case V3, or (2) measuring neutralizing antibodies Subjects immunized with different protocols are challenged with R5 viruses from various clades (A, B, C, etc.). Those that are primed with gp120-ABC and boosted with a mixture of V3-FPs (Group 304 above) have the most solid and broadest protection.

While gene gun immunization appears to be the most effective approach in priming anti-Env antibody responses, both intramuscular (IM) and intradermal (ID) routes are able to prime and induce IgG responses soon after one protein boost. Responses to ID administration appear more variable than the IM injection group. The antibody responses remain at relatively high level for more than 8 weeks after the last boost.

Thus, the present constructs are immunogenic in rabbits and are expected to be immunogenic in humans. Both IM and ID routes are effective in priming for a broadly neutralizing anti-V3 antibody response, similar to the gene gun approach. Protein boosts are highly effective in augmenting the antibody responses to peak levels in subjects primed with the present DNA compositions via the ID and IM routes.

Thus DNA immunization (priming) with a trivalent recombinant gp120 construct comprising three different V3 sequences induces an effective immune response against gp120 (focused on V3) from homologous and some heterologous strains of HIV-1. Recombinant V3-fusion proteins are effective in boosting the anti-V3 responses in all DNA-primed animals. This approach may therefore be use to prevent HIV infection and also to treat subjects already infected with HIV-1.

EXAMPLE III

Priming with gp120ABC DNA Induces Increased Antibody Titers

Rabbits were immunized with either codon optimized CA1 gp120 DNA immunogen or the recombinant gp120-ABC DNA immunogen of the invention in which V1/V2 was replaced by the Clade A consensus V3 loop sequence, V3 was replaced by a Clade B consensus V3 loop sequence and V4 was replaced by a Clade C consensus V3 loop sequence as described above (as in SEQ ID NO:8). As noted gp120-CA1 is the original amino sequence of gp120-CA1 of clade A.

The immunizing dose was given twice, 36 μg of either gp120-CA1 or gp120-ABC DNA. Boosting was with fusion proteins of V3 from clades A1, B and C (100 μg each).

Sera from immunized rabbits was tested for neutralization of pseudoviruses with consensus V3 sequences in the SF162 gp120 backbone. Results are shown in Table below.

TABLE 5

Neutralization of Pseudoviruses with Concensus V3 Sequences in SF162 gp120 backbone (Neutralizing titer)

| Priming DNA | Boost Protein | Animal # | SF 162 control | Clade A A/E | Clade A1 | Clade A A/G | Clade C | Clade C - glycan |
|---|---|---|---|---|---|---|---|---|
| gp120 ABC | V3-FP A/B/C | 1 | 725 | 4500 | 175 | 400 | 105 | 400 |
|  |  | 2 | 548 | 4900 | 370 | 360 | 145 | 360 |
|  |  | 3 | 603 | 6250 | 165 | 300 | 200 | 290 |
|  |  | 4 | 768 | 1000 | 325 | 150 | 350 | 170 |
|  |  | 5 | 663 | 3150 | 315 | 175 | 55 | 185 |
| CA1 | V3-FP A/B/C | 6 | 503 | 750 | 35 | <1:10 | 35 | <1:10 |
|  |  | 7 | 798 | 4100 | 490 | 300 | <1:10 | 290 |
|  |  | 8 | 248 | 400 | 16 | <1:10 | <1:10 | <1:10 |
|  |  | 9 | 123 | 12 | 40 | 20 | <1:10 | 20 |
|  |  | 10 | 888 | 110 | 120 | 125 | 25 | 140 |

The results indicate that the combination of the gp120-ABC priming and boosting with all 3 V3 fusion proteins the sequences of which were present in the priming DNA gave better and broader neutralizing responses against clade A (and subclade A1) and clade C V3 loop targets compared to priming with gp120 having a single V3 loop present in its sequence. This is also the first showing that chimeric psVs carrying clade C V3 can be neutralized.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A recombinant nucleic acid molecule that encodes a recombinant HIV-1 gp120 envelope polypeptide which is useful as an immunogen for priming an antibody response against V3 epitopes of the gp120 polypeptide in a mammal, said nucleic acid molecule comprising:

a nucleotide sequence that encodes a source gp120 polypeptide that has been genetically altered by insertion of a first and a second replacement nucleotide sequence each encoding a gp120 replacement V3 loop that is not native to the source gp120 polypeptide, wherein said first and said second encoded replacement V3 loop sequences replace native V1/V2 and V4 loops of the source gp120 polypeptide;

wherein each of said first and second replacement nucleotide sequences (i) is different from the other, and (ii) encodes a different replacement V3 loop peptide with a sequence of the same or of a distinct HIV-1 clade that is either the same as, or distinct from, the HIV-1 clade from which the source gp120 polypeptide was obtained, and wherein, upon administration to said mammal, the recombinant gp120 polypeptide primes said antibody response.

2. The nucleic acid molecule of claim 1, further comprising a third replacement nucleotide sequence that encodes a third replacement V3 loop which:

(a) is not native to, and is different in sequence from, the V3 loop of the source gp120 polypeptide; and (b) replaces the native V3 loop of the source gp120 polypeptide in the encoded recombinant gp120 envelope polypeptide.

3. The nucleic acid molecule of claim 1 that is a DNA plasmid.

4. The nucleic acid molecule of claim 2 that is a DNA plasmid.

5. The nucleic acid molecule of claim 2, wherein each replacement V3 loop is from HIV-1 clade A, B, C, D, E, F, G, H, I, J or K or a subclade of any of said clades.

6. The nucleic acid molecule of claim 5 wherein the nucleotide sequence encoding each replacement V3 loop encodes a consensus amino acid sequence of the V3 loop of HIV-1 clade A, B, C, D, E, F, G, H, I, J or K, or a subclade of any of said clades.

7. The nucleic acid molecule of claim 6 wherein the nucleotide sequence encoding each replacement V3 loop encodes a consensus amino acid sequence of the V3 loop of HIV-1 clade A, B or C.

8. The nucleic acid of claim 2, wherein the nucleotide sequence encoding the replacement V3 loops encodes a sequence that is (i) not a natural sequence of an HIV-1 isolate; and (ii) not a consensus amino acid sequence of a V3 loop of an HIV-1 clade.

9. The nucleic acid molecule of claim 6 wherein the V3 loop consensus amino acid sequence of HIV-1 clade A is of sub-clade A1.

10. The nucleic acid molecule of claim 2, wherein the source gp120 polypeptide is from a clade A HIV-1 isolate designated CA-1.

11. The nucleic acid molecule of claim 7 wherein the source gp120 polypeptide is from a clade A HIV-1 isolate designated CA-1.

12. The nucleic acid molecule of claim 2 which encodes a recombinant gp120 polypeptide in which the source gp120 variable loop sequences are replaced as follows:

(a) V1/V2 is replaced with a V3 loop sequence of sub-clade A1;

(b) V3 is replaced with a V3 loop sequence of clade B; and (c) V4 is replaced with a V3 loop sequence of clade C.

13. The nucleic acid molecule of claim 6 which encodes a recombinant gp120 polypeptide in which the source gp120 polypeptide variable loop sequences are replaced as follows:

(a) V1/V2 is replaced with a V3 having the consensus V3 sequence of subclade A1;

(b) V3 is replaced with a V3 loop having the consensus V3 sequence of clade B; and (c) V4 is replaced with a V3 loop having the consensus V3 sequence of clade C.

14. The nucleic acid molecule of claim 10 which encodes a recombinant gp120 polypeptide in which the source gp120 polypeptide variable loop sequences are replaced as follows:

(a) V1/V2 is replaced with a V3 having the consensus V3 sequence of subclade A1;

(b) V3 is replaced with a V3 loop having the consensus V3 sequence of clade B; and (c) V4 is replaced with a V3 loop having the consensus V3 sequence of clade C.

15. The nucleic acid molecule of claim 2 which is codon-optimized for expression in mammalian cells.

16. The nucleic acid molecule of claim 6 which is codon-optimized for expression in mammalian cells.

17. The nucleic acid molecule of claim 8 which is codon-optimized for expression in mammalian cells.

18. The nucleic acid molecule of claim 10 which is codon-optimized for expression in mammalian cells.

19. The nucleic acid molecule of claim 15 wherein the molecule is which is codon-optimized for expression in rabbit cells.

20. The nucleic acid molecule of claim 15 wherein the molecule is codon-optimized for expression in primate cells.

21. The nucleic acid molecule of claim 20 wherein the primate cells are human cells.

22. An immunogenic composition comprising the nucleic acid molecule of claim 2, and an immunologically and pharmaceutically acceptable carrier or excipient.

23. An immunogenic composition comprising the nucleic acid molecule of claim 6 and an immunologically and pharmaceutically acceptable carrier or excipient.

24. An immunogenic composition comprising the nucleic acid molecule of claim 12 and an immunologically and pharmaceutically acceptable carrier or excipient.

25. An immunogenic composition comprising the nucleic acid molecule of claim 13 and an immunologically and pharmaceutically acceptable carrier or excipient.

26. An immunogenic composition comprising the nucleic acid molecule of claim 21 and an immunologically and pharmaceutically acceptable carrier or excipient.

27. A method of priming a mammalian subject for an immune response against V3 epitopes of the HIV-1 gp120 polypeptide, comprising a administering to the subject an immunogenically effective amount of the immunogenic composition of claim 22 to prime said immune response.

28. A method of priming a mammalian subject for an immune response against V3 epitopes of the HIV-1 gp120 polypeptide, comprising a administering to the subject an immunogenically effective amount of the immunogenic composition of claim 23 to prime said immune response.

29. A method of priming a mammalian subject for an immune response against V3 epitopes of the HIV-1 gp120 polypeptide, comprising a administering to the subject an immunogenically effective amount of the immunogenic composition of claim 24 to prime said immune response.

30. The method of claim 27 wherein the subject is one who is susceptible to, or at risk of, HIV-1 infection.

31. The method of claim 27 wherein the subject is one who is infected with HIV-1.

32. The method of claim 27 wherein the immunogenic composition is administered by needle-less jet injection, intradermal injection, intramuscular injection, or gene gun delivery.

33. The method of claim 27, wherein the immune response being primed is a cross clade antibody response.

34. A method for inducing a cross clade antibody response against V3 epitopes of the HIV-1 gp 120 polypeptide, comprising: (a) priming an immune response according to the method of claim 27; and (b) administering one or more boosting doses of a boosting V3 immunogen comprising the same V3 epitopes against which the priming is directed.

35. The method of any of claim 34 wherein the boosting immunogen is a polypeptide or peptide immunogen that comprises said V3 epitopes.

36. The method of claim 27 further comprising administering an adjuvant before, during, or after said priming.

37. The method of claim 27 wherein the mammalian subject is a rodent, a rabbit, a non-human primate, or a human.

38. The method of claim 36 wherein the mammalian subject is a human.

39. A kit comprising the nucleic acid molecule of claim 2, and instructions for administering the nucleic acid to a subject for priming said anti-V3 antibody response.

40. A kit comprising the immunogenic composition of claim 22, and instructions for administering the composition to a subject for priming said anti-V3 antibody response.

41. The kit of claim 40, further comprising a polypeptide or peptide molecule that comprises said V3 epitopes and instructions for administering the polypeptide or peptide to boost said anti-V3 antibody response.

42. The kit of claim 39 wherein the kit further comprises an adjuvant.

43. The kit of claim 41 wherein the kit further comprises an adjuvant.

* * * * *

SEQUENCE LISTING

<160> NUMBER OF SEQ ID NOS: 82

<210> SEQ ID NO 1
<211> LENGTH: 1395
<212> TYPE: DNA
<213> ORGANISM: Human immunodeficiency virus
<220> FEATURE:
<221> NAME/KEY: CDS
<222> LOCATION: (1)..(1395)

<400> SEQUENCE: 1

```
tgg gtc aca gtc tat tat ggg gta cct gtg tgg aga gat gca gat acc       48
Trp Val Thr Val Tyr Tyr Gly Val Pro Val Trp Arg Asp Ala Asp Thr
1               5                   10                  15 act ctc ttt tgt gcg tct gat gct aaa gca tat agt act gaa aaa cat       96
Thr Leu Phe Cys Ala Ser Asp Ala Lys Ala Tyr Ser Thr Glu Lys His
            20                  25                  30 aat gtc tgg gct aca cat gcc tgt gta ccc aca gac ccc gac cca caa      144
Asn Val Trp Ala Thr His Ala Cys Val Pro Thr Asp Pro Asp Pro Gln
        35                  40                  45 gag ata tat ctg gaa aat gta aca gaa aat ttt aac atg cgg aaa aat      192
Glu Ile Tyr Leu Glu Asn Val Thr Glu Asn Phe Asn Met Arg Lys Asn
    50                  55                  60 aac atg gta gaa cag atg cat gag gat ata atc agt tta tgg gat gaa      240
Asn Met Val Glu Gln Met His Glu Asp Ile Ile Ser Leu Trp Asp Glu
```

```
                65                  70                  75                  80 agc cta aaa cca tgt gta aag cta acc cct ctc tgt gtt act tta aac       288
Ser Leu Lys Pro Cys Val Lys Leu Thr Pro Leu Cys Val Thr Leu Asn
            85                  90                  95 tgt act gat gta aag act aag aat aga act gtg gaa gac caa gca gaa       336
Cys Thr Asp Val Lys Thr Lys Asn Arg Thr Val Glu Asp Gln Ala Glu
        100                 105                 110 ttg aaa aac tgt tct ttc aat gta acc aca gaa aga aat aat aag aaa       384
Leu Lys Asn Cys Ser Phe Asn Val Thr Thr Glu Arg Asn Asn Lys Lys
            115                 120                 125 aag aga gaa tac gcg ctt ttc tat aaa ctt gat gta gta cca att aac       432
Lys Arg Glu Tyr Ala Leu Phe Tyr Lys Leu Asp Val Val Pro Ile Asn
    130                 135                 140 gct aat aat aat agt act gca ggt gat tat atg cta ata aat tgt aat       480
Ala Asn Asn Asn Ser Thr Ala Gly Asp Tyr Met Leu Ile Asn Cys Asn
145                 150                 155                 160 gtt tca acc gtt aaa cag gct tgc cca aag gta acc ttt gag cca att       528
Val Ser Thr Val Lys Gln Ala Cys Pro Lys Val Thr Phe Glu Pro Ile
                165                 170                 175 ccc ata cat tat tgt gct cca gct ggt tat gcg att cta aag tgt aat       576
Pro Ile His Tyr Cys Ala Pro Ala Gly Tyr Ala Ile Leu Lys Cys Asn
            180                 185                 190 gaa act aat ttc aat gga aca ggg cca tgc aaa aat gtc acc aca gta       624
Glu Thr Asn Phe Asn Gly Thr Gly Pro Cys Lys Asn Val Thr Thr Val
        195                 200                 205 caa tgc aca cat gga atc aag cca gta gta tca act caa cta ctg tta       672
Gln Cys Thr His Gly Ile Lys Pro Val Val Ser Thr Gln Leu Leu Leu
    210                 215                 220 aat ggc agt cta gca gaa gag aag ata atg att aga tct gaa aac ttc       720
Asn Gly Ser Leu Ala Glu Glu Lys Ile Met Ile Arg Ser Glu Asn Phe
225                 230                 235                 240 aca gac aat act aaa aac ata ata gta cag ttt aac agt tct gta aga       768
Thr Asp Asn Thr Lys Asn Ile Ile Val Gln Phe Asn Ser Ser Val Arg
                245                 250                 255 att aat tgt acc aga cct aac aac aat aca aga aaa ggt ata cat ata       816
Ile Asn Cys Thr Arg Pro Asn Asn Asn Thr Arg Lys Gly Ile His Ile
            260                 265                 270 gga cca gga agg gct atc tat gca acg ggt gat ata ata ggg gat ata       864
Gly Pro Gly Arg Ala Ile Tyr Ala Thr Gly Asp Ile Ile Gly Asp Ile
        275                 280                 285 aga caa gca cat tgt aat gtc agt aca gca gat tgg aat aac act tta       912
Arg Gln Ala His Cys Asn Val Ser Thr Ala Asp Trp Asn Asn Thr Leu
    290                 295                 300 caa aag gta gct aag caa tta aga gag atc tac aac aaa aca ata atc       960
Gln Lys Val Ala Lys Gln Leu Arg Glu Ile Tyr Asn Lys Thr Ile Ile
305                 310                 315                 320 ttt act aaa cac tca gga ggg gat gta gaa att aca aca cat agc ttt      1008
Phe Thr Lys His Ser Gly Gly Asp Val Glu Ile Thr Thr His Ser Phe
                325                 330                 335 aat tgt gga gga gaa ttt ttc tat tgc aat aca tca aga ttg ttt caa      1056
Asn Cys Gly Gly Glu Phe Phe Tyr Cys Asn Thr Ser Arg Leu Phe Gln
            340                 345                 350 ggc aca tgg gac aag aaa aat gac act tgg aat tac cca ggg tca aat      1104
Gly Thr Trp Asp Lys Lys Asn Asp Thr Trp Asn Tyr Pro Gly Ser Asn
        355                 360                 365 gac aat gac act ata act ctc cca tgc aga ata aag caa att gta cat      1152
Asp Asn Asp Thr Ile Thr Leu Pro Cys Arg Ile Lys Gln Ile Val His
    370                 375                 380 atg tgg cag aga gta gga caa gca atg tat gcc cct ccc atc caa gga      1200
```

```
Met Trp Gln Arg Val Gly Gln Ala Met Tyr Ala Pro Pro Ile Gln Gly
385                 390                 395                 400 aaa ata gag tgt aaa tca aac att aca gga cta cta tta aca aga gat       1248
Lys Ile Glu Cys Lys Ser Asn Ile Thr Gly Leu Leu Leu Thr Arg Asp
            405                 410                 415 ggt ggg aat aaa aca caa aat gaa acc ttc aga cct aca gga gga gac       1296
Gly Gly Asn Lys Thr Gln Asn Glu Thr Phe Arg Pro Thr Gly Gly Asp
            420                 425                 430 atg agg gac aat tgg aga agt gaa tta tat aag tat aaa gta gta gaa       1344
Met Arg Asp Asn Trp Arg Ser Glu Leu Tyr Lys Tyr Lys Val Val Glu
            435                 440                 445 att aga cca cta gga gta gca ccc acc aag gca aaa aga aga gtg gtg       1392
Ile Arg Pro Leu Gly Val Ala Pro Thr Lys Ala Lys Arg Arg Val Val
    450                 455                 460 cag                                                                    1395
Gln
465

<210> SEQ ID NO 2
<211> LENGTH: 465
<212> TYPE: PRT
<213> ORGANISM: Human immunodeficiency virus

<400> SEQUENCE: 2

Trp Val Thr Val Tyr Tyr Gly Val Pro Val Trp Arg Asp Ala Asp Thr
1               5                   10                  15

Thr Leu Phe Cys Ala Ser Asp Ala Lys Ala Tyr Ser Thr Glu Lys His
            20                  25                  30

Asn Val Trp Ala Thr His Ala Cys Val Pro Thr Asp Pro Asp Pro Gln
        35                  40                  45

Glu Ile Tyr Leu Glu Asn Val Thr Glu Asn Phe Asn Met Arg Lys Asn
    50                  55                  60

Asn Met Val Glu Gln Met His Glu Asp Ile Ile Ser Leu Trp Asp Glu
65                  70                  75                  80

Ser Leu Lys Pro Cys Val Lys Leu Thr Pro Leu Cys Val Thr Leu Asn
                85                  90                  95

Cys Thr Asp Val Lys Thr Lys Asn Arg Thr Val Glu Asp Gln Ala Glu
            100                 105                 110

Leu Lys Asn Cys Ser Phe Asn Val Thr Thr Glu Arg Asn Asn Lys Lys
        115                 120                 125

Lys Arg Glu Tyr Ala Leu Phe Tyr Lys Leu Asp Val Val Pro Ile Asn
    130                 135                 140

Ala Asn Asn Asn Ser Thr Ala Gly Asp Tyr Met Leu Ile Asn Cys Asn
145                 150                 155                 160

Val Ser Thr Val Lys Gln Ala Cys Pro Lys Val Thr Phe Glu Pro Ile
                165                 170                 175

Pro Ile His Tyr Cys Ala Pro Ala Gly Tyr Ala Ile Leu Lys Cys Asn
            180                 185                 190

Glu Thr Asn Phe Asn Gly Thr Gly Pro Cys Lys Asn Val Thr Thr Val
        195                 200                 205

Gln Cys Thr His Gly Ile Lys Pro Val Val Ser Thr Gln Leu Leu Leu
    210                 215                 220

Asn Gly Ser Leu Ala Glu Glu Lys Ile Met Ile Arg Ser Glu Asn Phe
225                 230                 235                 240

Thr Asp Asn Thr Lys Asn Ile Ile Val Gln Phe Asn Ser Ser Val Arg
                245                 250                 255
```

-continued

```
Ile Asn Cys Thr Arg Pro Asn Asn Thr Arg Lys Gly Ile His Ile
            260                 265                 270
Gly Pro Gly Arg Ala Ile Tyr Ala Thr Gly Asp Ile Ile Gly Asp Ile
        275                 280                 285
Arg Gln Ala His Cys Asn Val Ser Thr Ala Asp Trp Asn Asn Thr Leu
    290                 295                 300
Gln Lys Val Ala Lys Gln Leu Arg Glu Ile Tyr Asn Lys Thr Ile Ile
305                 310                 315                 320
Phe Thr Lys His Ser Gly Gly Asp Val Glu Ile Thr Thr His Ser Phe
                325                 330                 335
Asn Cys Gly Gly Glu Phe Phe Tyr Cys Asn Thr Ser Arg Leu Phe Gln
            340                 345                 350
Gly Thr Trp Asp Lys Lys Asn Asp Thr Trp Asn Tyr Pro Gly Ser Asn
        355                 360                 365
Asp Asn Asp Thr Ile Thr Leu Pro Cys Arg Ile Lys Gln Ile Val His
    370                 375                 380
Met Trp Gln Arg Val Gly Gln Ala Met Tyr Ala Pro Pro Ile Gln Gly
385                 390                 395                 400
Lys Ile Glu Cys Lys Ser Asn Ile Thr Gly Leu Leu Leu Thr Arg Asp
                405                 410                 415
Gly Gly Asn Lys Thr Gln Asn Glu Thr Phe Arg Pro Thr Gly Gly Asp
            420                 425                 430
Met Arg Asp Asn Trp Arg Ser Glu Leu Tyr Lys Tyr Lys Val Val Glu
        435                 440                 445
Ile Arg Pro Leu Gly Val Ala Pro Thr Lys Ala Lys Arg Arg Val Val
    450                 455                 460
Gln
465

<210> SEQ ID NO 3
<211> LENGTH: 105
<212> TYPE: DNA
<213> ORGANISM: Artificial Sequence
<220> FEATURE:
<223> OTHER INFORMATION: Synthetic sequence

<400> SEQUENCE: 3
tgcacccgcc ccaacaacaa cacccgcaag agcatccgca tcggccctgg ccaggccttc      60
tacgccaccg gcgacatcat cggcgacatc cgccaggccc actgc                    105

<210> SEQ ID NO 4
<211> LENGTH: 105
<212> TYPE: DNA
<213> ORGANISM: Artificial Sequence
<220> FEATURE:
<223> OTHER INFORMATION: Synthetic Sequence

<400> SEQUENCE: 4
tgtacaagac ccaacaacaa tacaagaaaa agtatacaca taggaccagg gagagcattc      60
tatacaacag gagaaataat aggagatata agacaagcac attgt                    105

<210> SEQ ID NO 5
<211> LENGTH: 105
<212> TYPE: DNA
<213> ORGANISM: Artificial Sequence
<220> FEATURE:
<223> OTHER INFORMATION: Synthetic Sequence

<400> SEQUENCE: 5
```

```
tgtacaagac ccaacaataa tacaagaaaa agtataagga taggaccagg acaaacattc    60
tatgcaacag gagacataat aggagacata agacaagcac attgt                  105
```

<210> SEQ ID NO 6
<211> LENGTH: 1317
<212> TYPE: DNA
<213> ORGANISM: Artificial Sequence
<220> FEATURE:
<223> OTHER INFORMATION: Synthetic Sequence

<400> SEQUENCE: 6

```
tgggtgaccg tgtactacgg cgtgcccgtg tggagagatg ccgacaccac cctgttctgc    60
gccagcgacg ccaaggccta cagcaccgag aagcacaatg tgtgggccac ccacgcctgc   120
gtgcccaccg accccgaccc ccaggagatc tacctggaga acgtgaccga gaacttcaac   180
atgcgcaaga caacatggt ggagcagatg cacgaggaca tcatcagcct gtgggacgag   240
agcctgaagc cttgcgtgaa gctgacccct ctgtgcgtga ccctgaactg cacccgcccc   300
aacaacaaca cccgcaagag catccgcatc ggccctggcc aggccttcta cgccaccggc   360
gacatcatcg gcgacatccg ccaggcccac tgcaacgtga gcaccgtgaa gcaggcctgc   420
cccaaagtga ccttcgagcc catccccatc cactactgcg cccctgccgg ctacgccatc   480
ctgaagtgca acgagaccaa cttcaacggc accggcccct gcaagaatgt gaccaccgtg   540
cagtgcaccc acggcatcaa gcccgtggtg agcacccagc tgctgctgaa cggcagcctg   600
gccgaggaga agatcatgat ccggagcgag aatttcaccg acaacaccaa gaacatcatc   660
gtgcagttca cagcagcgt gcgcatcaat tgtacaagac ccaacaacaa tacaagaaaa   720
agtatacaca taggaccagg gagagcattc tatacaacag gagaaataat aggagatata   780
agacaagcac attgtaatgt gtctaccgcc gactggaaca caccctgca gaaagtggcc   840 aagcagctgc gggagatcta caacaagacc atcatcttca ccaagcacag cggcggagat   900
gtggagatca ccacccacag cttcaattgt ggcggcgagt tcttctactg tacaagaccc   960
aacaataata caagaaaaag tataaggata ggaccaggac aaacattcta tgcaacagga  1020
gacataatag gagacataag acaagcacat tgtcggatca agcagatcgt gcacatgtgg  1080
cagcgcgtgg gccaggccat gtacgccct cccatccagg caagatcga gtgcaagagc  1140 aacatcaccg gcctgctgct gaccagagat ggcggcaaca agacccagaa cgagaccttc  1200
agacccacag cggcgacat gagggacaac tggcggagcg agctgtacaa gtacaaagtg  1260
gtggagatca gacccctggg cgtggccccc accaaggcca agagaagagt ggtgcag     1317
```

<210> SEQ ID NO 7
<211> LENGTH: 1344
<212> TYPE: DNA
<213> ORGANISM: Artificial Sequence
<220> FEATURE:
<223> OTHER INFORMATION: Synthetic Sequence

<400> SEQUENCE: 7

```
ggtaccgcta gctgggtgac cgtgtactac ggcgtgcccg tgtggagaga tgccgacacc    60
accctgttct gcgccagcga cgccaaggcc tacagcaccg agaagcacaa tgtgtgggcc   120
acccacgcct gcgtgcccac cgaccccgac ccccaggaga tctacctgga gaacgtgacc   180
gagaacttca catgcgcaa gaacaacatg tggagcaga tgcacgagga catcatcagc   240
ctgtgggacg agagcctgaa gccttgcgtg aagctgaccc tctgtgcgt gaccctgaac   300
```

-continued

```
tgcacccgcc ccaacaacaa cacccgcaag agcatccgca tcggccctgg ccaggccttc      360
tacgccaccg gcgacatcat cggcgacatc cgccaggccc actgcaacgt gagcaccgtg      420
aagcaggcct gccccaaagt gaccttcgag cccatcccca tccactactg cgcccctgcc      480
ggctacgcca tcctgaagtg caacgagacc aacttcaacg gcaccggccc ctgcaagaat      540
gtgaccaccg tgcagtgcac ccacggcatc aagcccgtgg tgagcaccca gctgctgctg      600
aacggcagcc tggccgagga agatcatg atccggagcg agaatttcac cgacaacacc        660
aagaacatca tcgtgcagtt caacagcagc gtgcgcatca attgtacaag acccaacaac      720
aatacaagaa aaagtataca cataggacca gggagagcat tctatacaac aggagaaata      780
ataggagata taagacaagc acattgtaat gtgtctaccg ccgactggaa caacaccctg      840
cagaaagtgg ccaagcagct gcgggagatc tacaacaaga ccatcatctt caccaagcac      900
agcggcggag atgtggagat caccacccac agcttcaatt gtggcggcga gttcttctac      960
tgtacaagac ccaacaataa tacaagaaaa agtataagga taggaccagg acaaacattc     1020
tatgcaacag agacataat aggagacata agacaagcac attgtcggat caagcagatc      1080
gtgcacatgt ggcagcgcgt gggccaggcc atgtacgccc ctcccatcca gggcaagatc     1140
gagtgcaaga gcaacatcac cggcctgctg ctgaccagag atggcggcaa caagacccag     1200
aacgagacct tcagacccac aggcggcgac atgagggaca actggcggag cgagctgtac     1260
aagtacaaag tggtggagat cagacccctg ggcgtggccc ccaccaaggc caagagaaga     1320
gtggtgcagt gaggatccga gctc                                           1344
```

<210> SEQ ID NO 8
<211> LENGTH: 439
<212> TYPE: PRT
<213> ORGANISM: Artificial Sequence
<220> FEATURE:
<223> OTHER INFORMATION: Synthetic Sequence

<400> SEQUENCE: 8

```
Trp Val Thr Val Tyr Tyr Gly Val Pro Val Trp Arg Asp Ala Asp Thr
1               5                   10                  15

Thr Leu Phe Cys Ala Ser Asp Ala Lys Ala Tyr Ser Thr Glu Lys His
            20                  25                  30

Asn Val Trp Ala Thr His Ala Cys Val Pro Thr Asp Pro Asp Pro Gln
        35                  40                  45

Glu Ile Tyr Leu Glu Asn Val Thr Glu Asn Phe Asn Met Arg Lys Asn
    50                  55                  60

Asn Met Val Glu Gln Met His Glu Asp Ile Ile Ser Leu Trp Asp Glu
65                  70                  75                  80

Ser Leu Lys Pro Cys Val Lys Leu Thr Pro Leu Cys Val Thr Leu Asn
                85                  90                  95

Cys Thr Arg Pro Asn Asn Thr Arg Lys Ser Ile Arg Ile Gly Pro
            100                 105                 110

Gly Gln Ala Phe Tyr Ala Thr Gly Asp Ile Ile Gly Asp Ile Arg Gln
        115                 120                 125

Ala His Cys Asn Val Ser Thr Val Lys Gln Ala Cys Pro Lys Val Thr
    130                 135                 140

Phe Glu Pro Ile Pro Ile His Tyr Cys Ala Pro Ala Gly Tyr Ala Ile
145                 150                 155                 160

Leu Lys Cys Asn Glu Thr Asn Phe Asn Gly Thr Gly Pro Cys Lys Asn
                165                 170                 175
```

-continued

Val Thr Thr Val Gln Cys Thr His Gly Ile Lys Pro Val Val Ser Thr
            180                 185                 190

Gln Leu Leu Leu Asn Gly Ser Leu Ala Glu Glu Lys Ile Met Ile Arg
        195                 200                 205

Ser Glu Asn Phe Thr Asp Asn Thr Lys Asn Ile Ile Val Gln Phe Asn
    210                 215                 220

Ser Ser Val Arg Ile Asn Cys Thr Arg Pro Asn Asn Asn Thr Arg Lys
225                 230                 235                 240

Ser Ile His Ile Gly Pro Gly Arg Ala Phe Tyr Thr Thr Gly Glu Ile
                245                 250                 255

Ile Gly Asp Ile Arg Gln Ala His Cys Asn Val Ser Thr Ala Asp Trp
            260                 265                 270

Asn Asn Thr Leu Gln Lys Val Ala Lys Gln Leu Arg Glu Ile Tyr Asn
        275                 280                 285

Lys Thr Ile Ile Phe Thr Lys His Ser Gly Gly Asp Val Glu Ile Thr
    290                 295                 300

Thr His Ser Phe Asn Cys Gly Gly Glu Phe Phe Tyr Cys Thr Arg Pro
305                 310                 315                 320

Asn Asn Asn Thr Arg Lys Ser Ile Arg Ile Gly Pro Gly Gln Thr Phe
                325                 330                 335

Tyr Ala Thr Gly Asp Ile Ile Gly Asp Ile Arg Gln Ala His Cys Arg
            340                 345                 350

Ile Lys Gln Ile Val His Met Trp Gln Arg Val Gly Gln Ala Met Tyr
        355                 360                 365

Ala Pro Pro Ile Gln Gly Lys Ile Glu Cys Lys Ser Asn Ile Thr Gly
    370                 375                 380

Leu Leu Leu Thr Arg Asp Gly Gly Asn Lys Thr Gln Asn Glu Thr Phe
385                 390                 395                 400

Arg Pro Thr Gly Gly Asp Met Arg Asp Asn Trp Arg Ser Glu Leu Tyr
                405                 410                 415

Lys Tyr Lys Val Val Glu Ile Arg Pro Leu Gly Val Ala Pro Thr Lys
            420                 425                 430

Ala Lys Arg Arg Val Val Gln
        435

<210> SEQ ID NO 9
<211> LENGTH: 447
<212> TYPE: PRT
<213> ORGANISM: Artificial Sequence
<220> FEATURE:
<223> OTHER INFORMATION: Synthetic Sequence

<400> SEQUENCE: 9

Gly Thr Ala Ser Trp Val Thr Val Tyr Tyr Gly Val Pro Val Trp Arg
1               5                   10                  15

Asp Ala Asp Thr Thr Leu Phe Cys Ala Ser Asp Ala Lys Ala Tyr Ser
            20                  25                  30

Thr Glu Lys His Asn Val Trp Ala Thr His Ala Cys Val Pro Thr Asp
        35                  40                  45

Pro Asp Pro Gln Glu Ile Tyr Leu Glu Asn Val Thr Glu Asn Phe Asn
    50                  55                  60

Met Arg Lys Asn Asn Met Val Glu Gln Met His Glu Asp Ile Ile Ser
65                  70                  75                  80

Leu Trp Asp Glu Ser Leu Lys Pro Cys Val Lys Leu Thr Pro Leu Cys
                85                  90                  95

```
Val Thr Leu Asn Cys Thr Arg Pro Asn Asn Thr Arg Lys Ser Ile
            100                 105                 110

Arg Ile Gly Pro Gly Gln Ala Phe Tyr Ala Thr Gly Asp Ile Ile Gly
        115                 120                 125

Asp Ile Arg Gln Ala His Cys Asn Val Ser Thr Val Lys Gln Ala Cys
    130                 135                 140

Pro Lys Val Thr Phe Glu Pro Ile Pro Ile His Tyr Cys Ala Pro Ala
145                 150                 155                 160

Gly Tyr Ala Ile Leu Lys Cys Asn Glu Thr Asn Phe Asn Gly Thr Gly
                165                 170                 175

Pro Cys Lys Asn Val Thr Val Gln Cys Thr His Gly Ile Lys Pro
        180                 185                 190

Val Val Ser Thr Gln Leu Leu Leu Asn Gly Ser Leu Ala Glu Glu Lys
        195                 200                 205

Ile Met Ile Arg Ser Glu Asn Phe Thr Asp Asn Thr Lys Asn Ile Ile
    210                 215                 220

Val Gln Phe Asn Ser Ser Val Arg Ile Asn Cys Thr Arg Pro Asn Asn
225                 230                 235                 240

Asn Thr Arg Lys Ser Ile His Ile Gly Pro Gly Arg Ala Phe Tyr Thr
                245                 250                 255

Thr Gly Glu Ile Ile Gly Asp Ile Arg Gln Ala His Cys Asn Val Ser
        260                 265                 270

Thr Ala Asp Trp Asn Asn Thr Leu Gln Lys Val Ala Lys Gln Leu Arg
        275                 280                 285

Glu Ile Tyr Asn Lys Thr Ile Ile Phe Thr Lys His Ser Gly Gly Asp
        290                 295                 300

Val Glu Ile Thr Thr His Ser Phe Asn Cys Gly Gly Glu Phe Phe Tyr
305                 310                 315                 320

Cys Thr Arg Pro Asn Asn Asn Thr Arg Lys Ser Ile Arg Ile Gly Pro
                325                 330                 335

Gly Gln Thr Phe Tyr Ala Thr Gly Asp Ile Ile Gly Asp Ile Arg Gln
            340                 345                 350

Ala His Cys Arg Ile Lys Gln Ile Val His Met Trp Gln Arg Val Gly
        355                 360                 365

Gln Ala Met Tyr Ala Pro Pro Ile Gln Gly Lys Ile Glu Cys Lys Ser
    370                 375                 380

Asn Ile Thr Gly Leu Leu Leu Thr Arg Asp Gly Gly Asn Lys Thr Gln
385                 390                 395                 400

Asn Glu Thr Phe Arg Pro Thr Gly Gly Asp Met Arg Asp Asn Trp Arg
                405                 410                 415

Ser Glu Leu Tyr Lys Tyr Lys Val Val Glu Ile Arg Pro Leu Gly Val
            420                 425                 430

Ala Pro Thr Lys Ala Lys Arg Arg Val Val Gln Gly Ser Glu Leu
        435                 440                 445

<210> SEQ ID NO 10
<211> LENGTH: 35
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (10)..(10)
<223> OTHER INFORMATION: The Xaa at position 10 can be any amino acid
<220> FEATURE:
<221> NAME/KEY: MISC_FEATURE
```

```
<222> LOCATION: (12)..(13)
<223> OTHER INFORMATION: The Xaa at positions 12-13 can be any amino
      acid
<220> FEATURE:
<221> NAME/KEY: MISC_FEATURE
<222> LOCATION: (18)..(20)
<223> OTHER INFORMATION: The Xaa at positions 18-20 can be any amino
      acid
<220> FEATURE:
<221> NAME/KEY: MISC_FEATURE
<222> LOCATION: (34)..(34)
<223> OTHER INFORMATION: The Xaa at position 34 can be any amino acid

<400> SEQUENCE: 10

Cys Thr Arg Pro Asp Asn Asn Thr Arg Xaa Thr Xaa Xaa Ile Gly Pro
1               5                   10                  15

Gly Xaa Xaa Xaa Tyr Ala Thr Gly Asp Ile Ile Gly Asp Ile Arg Gln
            20                  25                  30

Ala Xaa Cys
        35

<210> SEQ ID NO 11
<211> LENGTH: 35
<212> TYPE: PRT
<213> ORGANISM: Human immunodeficiency virus

<400> SEQUENCE: 11

Cys Thr Arg Pro Asn Asn Asn Thr Arg Lys Ser Ile Asn Ile Ala Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 12
<211> LENGTH: 35
<212> TYPE: PRT
<213> ORGANISM: Human immunodeficiency virus

<400> SEQUENCE: 12

Cys Thr Arg Pro Asn Asn Asn Thr Arg Lys Ser Ile His Ile Gln Pro
1               5                   10                  15

Gly Arg Ala Phe Tyr Ala Thr Gly Glu Ile Ile Gly Asp Ile Arg Gln
            20                  25                  30

Ala His Cys
        35

<210> SEQ ID NO 13
<211> LENGTH: 35
<212> TYPE: PRT
<213> ORGANISM: Human immunodeficiency virus

<400> SEQUENCE: 13

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 14
<211> LENGTH: 35
<212> TYPE: PRT
```

-continued

<213> ORGANISM: Human immunodeficiency virus

<400> SEQUENCE: 14

Cys Thr Arg Pro Asn Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

<210> SEQ ID NO 15
<211> LENGTH: 35
<212> TYPE: PRT
<213> ORGANISM: Human immunodeficiency virus

<400> SEQUENCE: 15

Cys Ile Arg Pro Asn Asn Asn Thr Arg Lys Ser Ile His Met Gly Pro
1               5                   10                  15

Gly Arg Ala Phe Tyr Ala Thr Gly Asp Ile Ile Gly Asn Ile Arg Gln
            20                  25                  30

Ala His Cys
        35

<210> SEQ ID NO 16
<211> LENGTH: 35
<212> TYPE: PRT
<213> ORGANISM: Human immunodeficiency virus

<400> SEQUENCE: 16

Cys Val Arg Pro Asn Asn Asn Thr Arg Lys Ser Ile His Ile Gly Pro
1               5                   10                  15

Gly Gln Ala Phe Tyr Ala Thr Gly Asp Ile Ile Gly Asn Ile Arg Gln
            20                  25                  30

Ala His Cys
        35

<210> SEQ ID NO 17
<211> LENGTH: 35
<212> TYPE: PRT
<213> ORGANISM: Human immunodeficiency virus

<400> SEQUENCE: 17

Cys Thr Arg Pro Asn Asn Asn Thr Arg Lys Ser Ile His Ile Gly Pro
1               5                   10                  15

Gly Gln Ala Phe Tyr Ala Thr Gly Asp Ile Ile Gly Asn Ile Arg Gln
            20                  25                  30

Ala His Cys
        35

<210> SEQ ID NO 18
<211> LENGTH: 35
<212> TYPE: PRT
<213> ORGANISM: Human immunodeficiency virus

<400> SEQUENCE: 18

Cys Thr Arg Pro Asn Asn Asn Thr Arg Lys Ser Val His Ile Gly Pro
1               5                   10                  15

Gly Arg Ala Phe Tyr Gly Ile Gly Asp Ile Ile Gly Asn Ile Arg Gln
            20                  25                  30

Ala His Cys

-continued

```
                35

<210> SEQ ID NO 19
<211> LENGTH: 35
<212> TYPE: PRT
<213> ORGANISM: Human immunodeficiency virus

<400> SEQUENCE: 19

Cys Thr Arg Pro Asn Asn Asn Thr Arg Lys Gly Val His Ile Gly Pro
1               5                   10                  15

Gly Arg Thr Phe Tyr Ala Thr Gly Glu Ile Ile Gly Asn Ile Arg Gln
            20                  25                  30

Ala His Cys
        35

<210> SEQ ID NO 20
<211> LENGTH: 35
<212> TYPE: PRT
<213> ORGANISM: Human immunodeficiency virus

<400> SEQUENCE: 20

Cys Thr Arg Pro Asn Asn Asn Thr Arg Lys Gly Ile His Ile Gly Pro
1               5                   10                  15

Gly Arg Thr Phe Tyr Ala Thr Asp Ala Ile Ile Gly Asn Ile Arg Gln
            20                  25                  30

Ala His Cys
        35

<210> SEQ ID NO 21
<211> LENGTH: 35
<212> TYPE: PRT
<213> ORGANISM: Human immunodeficiency virus

<400> SEQUENCE: 21

Cys Thr Arg Pro Asn Asn Asn Thr Arg Lys Gly Ile Asn Met Gly Pro
1               5                   10                  15

Gly Arg Ala Phe Tyr Ala Thr Asp Ile Val Gly Asp Ile Ile Gln
            20                  25                  30

Ala His Cys
        35

<210> SEQ ID NO 22
<211> LENGTH: 35
<212> TYPE: PRT
<213> ORGANISM: Human immunodeficiency virus

<400> SEQUENCE: 22

Cys Thr Arg Pro Asn Asn Asn Thr Arg Thr Gly Val His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

<210> SEQ ID NO 23
<211> LENGTH: 35
<212> TYPE: PRT
<213> ORGANISM: Human immunodeficiency virus

<400> SEQUENCE: 23

Cys Ile Arg Pro Asn Asn Asn Thr Arg Lys Ser Ile Arg Ile Gly Pro
```

```
                1               5                  10                 15
Gly Gln Ala Phe Tyr Ala Arg Gly Asp Val Ile Ser Asn Ile Arg His
                20                 25                 30

Ala Tyr Cys
        35

<210> SEQ ID NO 24
<211> LENGTH: 35
<212> TYPE: PRT
<213> ORGANISM: Human immunodeficiency virus

<400> SEQUENCE: 24

Cys Ile Arg Pro Asn Asn Asn Thr Arg Lys Ser Ile His Ile Gly Pro
1               5                  10                 15

Gly Gln Ala Phe Tyr Ala Arg Gly Asp Ile Ile Gly Asn Ile Arg Gln
                20                 25                 30

Ala Tyr Cys
        35

<210> SEQ ID NO 25
<211> LENGTH: 35
<212> TYPE: PRT
<213> ORGANISM: Human immunodeficiency virus

<400> SEQUENCE: 25

Cys Val Arg Pro Asn Asn Asn Thr Arg Arg Ser Ile His Ile Gly Pro
1               5                  10                 15

Gly Gln Ala Leu Tyr Ala Thr Gly Arg Ile Ile Gly Asn Ile Arg Gln
                20                 25                 30

Ala Tyr Cys
        35

<210> SEQ ID NO 26
<211> LENGTH: 35
<212> TYPE: PRT
<213> ORGANISM: Human immunodeficiency virus

<400> SEQUENCE: 26

Cys Ile Arg Gly Asn Asn Asn Thr Arg Lys Ser Met Arg Ile Gly Pro
1               5                  10                 15

Gly Gln Ala Phe Tyr Ala Thr Gly Asp Ile Ile Gly Asp Ile Arg Arg
                20                 25                 30

Ala Tyr Cys
        35

<210> SEQ ID NO 27
<211> LENGTH: 35
<212> TYPE: PRT
<213> ORGANISM: Human immunodeficiency virus

<400> SEQUENCE: 27

Cys Ile Arg Gly Asn Asn Asn Thr Arg Lys Ser Val Arg Ile Gly Pro
1               5                  10                 15

Gly Gln Thr Phe Tyr Thr His Gly Ala Ile Ile Gly Asp Ile Arg Gln
                20                 25                 30

Ala His Cys
        35

<210> SEQ ID NO 28
<211> LENGTH: 34
```

```
<212> TYPE: PRT
<213> ORGANISM: Human immunodeficiency virus

<400> SEQUENCE: 28

Cys Thr Arg Pro Gly Asn Asn Thr Arg Ser Ile Ser Ile Gly Pro
1               5                   10                  15

Gly Gln Ala Phe Tyr Thr Thr Asp Ile Ile Gly Asp Ile Arg Gln Ala
            20                  25                  30

Tyr Cys

<210> SEQ ID NO 29
<211> LENGTH: 35
<212> TYPE: PRT
<213> ORGANISM: Human immunodeficiency virus

<400> SEQUENCE: 29

Cys Ile Arg Pro Asn Asn Asn Thr Arg Lys Ser Ile Pro Ile Gly Pro
1               5                   10                  15

Gly Arg Ala Phe Tyr Ala Thr Gly Asp Ile Ile Gly Asp Ile Arg Lys
            20                  25                  30

Ala Tyr Cys
        35

<210> SEQ ID NO 30
<211> LENGTH: 35
<212> TYPE: PRT
<213> ORGANISM: Human immunodeficiency virus

<400> SEQUENCE: 30

Cys Ser Arg Pro Asn Asn Asn Thr Arg Lys Ser Ile His Ile Gly Pro
1               5                   10                  15

Gly Arg Ala Phe Tyr Ala Thr Asp Asp Ile Ile Gly Asn Ile Arg Gln
            20                  25                  30

Ala Tyr Cys
        35

<210> SEQ ID NO 31
<211> LENGTH: 35
<212> TYPE: PRT
<213> ORGANISM: Human immunodeficiency virus

<400> SEQUENCE: 31

Cys Thr Arg Pro Gly Asn Asn Thr Arg Lys Ser Ile Arg Ile Gly Pro
1               5                   10                  15

Gly Gln Thr Phe Tyr Ala Thr Gly Asp Ile Ile Gly Asn Ile Arg Gln
            20                  25                  30

Ala His Cys
        35

<210> SEQ ID NO 32
<211> LENGTH: 35
<212> TYPE: PRT
<213> ORGANISM: Human immunodeficiency virus

<400> SEQUENCE: 32

Cys Thr Arg Pro Gly Asn Asn Thr Arg Lys Ser Val Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
```

-continued

```
                35

<210> SEQ ID NO 33
<211> LENGTH: 35
<212> TYPE: PRT
<213> ORGANISM: Human immunodeficiency virus

<400> SEQUENCE: 33

Cys Thr Arg Pro Gly Ser Asn Thr Arg Lys Ser Ile Arg Ile Gly Pro
1               5                   10                  15

Gly Gln Ala Phe Tyr Ala Thr Gly Asp Val Ile Gly Asp Ile Arg Glu
            20                  25                  30

Ala Ser Cys
        35

<210> SEQ ID NO 34
<211> LENGTH: 35
<212> TYPE: PRT
<213> ORGANISM: Human immunodeficiency virus

<400> SEQUENCE: 34

Cys Thr Arg Pro Gly Asn Asn Thr Arg Lys Ser Ile Arg Ile Gly Pro
1               5                   10                  15

Gly Gln Val Leu Tyr Ala Thr Gly Glu Ile Ile Gly Glu Ile Arg Gln
            20                  25                  30

Ala Tyr Cys
        35

<210> SEQ ID NO 35
<211> LENGTH: 35
<212> TYPE: PRT
<213> ORGANISM: Human immunodeficiency virus

<400> SEQUENCE: 35

Cys Thr Arg Pro Asn Asn Asn Thr Arg Lys Ser Val Arg Ile Gly Pro
1               5                   10                  15

Gly Gln Thr Phe Tyr Ala Thr Gly Asp Ile Ile Gly Glu Ile Arg Gln
            20                  25                  30

Ala Tyr Cys
        35

<210> SEQ ID NO 36
<211> LENGTH: 35
<212> TYPE: PRT
<213> ORGANISM: Human immunodeficiency virus

<400> SEQUENCE: 36

Cys Thr Arg Pro Asn Asn Asn Thr Arg Glu Ser Val Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 37
<211> LENGTH: 35
<212> TYPE: PRT
<213> ORGANISM: Human immunodeficiency virus

<400> SEQUENCE: 37

Cys Thr Arg Pro Asn Asn Asn Thr Arg Arg Ser Ile Gly Ile Gly Pro
```

-continued

```
                1               5                  10                 15
Gly Gln Thr Ile Tyr Ala Thr Gly Ala Ile Ile Gly Asp Ile Arg Gln
                20                    25                 30

Ala His Cys
        35

<210> SEQ ID NO 38
<211> LENGTH: 35
<212> TYPE: PRT
<213> ORGANISM: Human immunodeficiency virus

<400> SEQUENCE: 38

Cys Thr Arg Pro Ser Asn Asn Thr Arg Lys Gly Trp His Ile Gly Pro
1               5                   10                  15

Gly Gln Thr Leu Tyr Ala Thr Gly Ala Ile Ile Gly Asp Ile Arg Gln
                20                    25                 30

Ala His Cys
        35

<210> SEQ ID NO 39
<211> LENGTH: 35
<212> TYPE: PRT
<213> ORGANISM: Human immunodeficiency virus

<400> SEQUENCE: 39

Cys Thr Arg Pro Asn Asn Asn Thr Arg Lys Ser Ile Arg Ile Gly Pro
1               5                   10                  15

Gly Gln Ala Leu Tyr Ala Thr Gly Ala Ile Ile Gly Asn Ile Arg Gln
                20                    25                 30

Ala His Cys
        35

<210> SEQ ID NO 40
<211> LENGTH: 35
<212> TYPE: PRT
<213> ORGANISM: Human immunodeficiency virus

<400> SEQUENCE: 40

Cys Thr Arg Pro Asn Asn Asn Thr Arg Lys Ser Ile Gly Ile Gly Pro
1               5                   10                  15

Gly Gln Val Phe Tyr Ala Thr Gly Asp Ile Ile Gly Asp Ile Arg Gln
                20                    25                 30

Ala His Cys
        35

<210> SEQ ID NO 41
<211> LENGTH: 35
<212> TYPE: PRT
<213> ORGANISM: Human immunodeficiency virus

<400> SEQUENCE: 41

Cys Thr Arg Pro Gly Asn Asn Thr Arg Lys Gly Ile Gly Ile Gly Pro
1               5                   10                  15

Gly Gln Met Phe Tyr Ala Thr Gly Ser Ile Ile Gly Asp Ile Arg Gln
                20                    25                 30

Ala His Cys
        35

<210> SEQ ID NO 42
<211> LENGTH: 35
```

```
<212> TYPE: PRT
<213> ORGANISM: Human immunodeficiency virus

<400> SEQUENCE: 42

Cys Thr Arg Pro Asn Asn Asn Thr Arg Ser Ile Pro Met Gly Pro
1               5                   10                  15

Gly Lys Ala Phe Tyr Ala Thr Gly Asp Ile Ile Gly Asp Ile Arg Gln
            20                  25                  30

Ala His Cys
        35

<210> SEQ ID NO 43
<211> LENGTH: 35
<212> TYPE: PRT
<213> ORGANISM: Human immunodeficiency virus

<400> SEQUENCE: 43

Cys Thr Arg Pro Ser Asn Asn Thr Arg Lys Ser Ile Pro Ile Gly Pro
1               5                   10                  15

Gly Gln Ala Ile Tyr Ala Thr Gly Glu Ile Ile Gly Asp Ile Arg Lys
            20                  25                  30

Ala His Cys
        35

<210> SEQ ID NO 44
<211> LENGTH: 35
<212> TYPE: PRT
<213> ORGANISM: Human immunodeficiency virus

<400> SEQUENCE: 44

Cys Thr Arg Pro Asn Asn Asn Thr Arg Lys Ser Ile His Met Gly Pro
1               5                   10                  15

Gly Gln Ala Met Tyr Val Thr Gly Asp Ile Ile Gly Asp Ile Arg Arg
            20                  25                  30

Ala His Cys
        35

<210> SEQ ID NO 45
<211> LENGTH: 35
<212> TYPE: PRT
<213> ORGANISM: Human immunodeficiency virus

<400> SEQUENCE: 45

Cys Thr Arg Pro Asn Asn Asn Thr Arg Glu Ser Ile Arg Ile Gly Pro
1               5                   10                  15

Gly Gln Thr Phe Tyr Ala Thr Gly Asp Ile Ile Gly Asp Ile Arg Gln
            20                  25                  30

Ala His Cys
        35

<210> SEQ ID NO 46
<211> LENGTH: 35
<212> TYPE: PRT
<213> ORGANISM: Human immunodeficiency virus

<400> SEQUENCE: 46

Cys Thr Arg Pro Asn Asn Asn Thr Arg Lys Ser Ile Arg Ile Gly Pro
1               5                   10                  15

Gly Gln Thr Phe Tyr Ala Thr Gly Asp Ile Ile Gly Asp Ile Arg Gln
            20                  25                  30
```

Ala His Cys
        35

<210> SEQ ID NO 47
<211> LENGTH: 35
<212> TYPE: PRT
<213> ORGANISM: Human immunodeficiency virus

<400> SEQUENCE: 47

Cys Thr Arg Pro Asn Asn Thr Arg Lys Ser Ile Arg Ile Gly Pro
1               5                   10                  15

Gly Gln Val Phe Tyr Ala Thr Gly Asp Ile Ile Gly Asp Ile Arg Gln
            20                  25                  30

Ala His Cys
        35

<210> SEQ ID NO 48
<211> LENGTH: 35
<212> TYPE: PRT
<213> ORGANISM: Human immunodeficiency virus

<400> SEQUENCE: 48

Cys Ile Arg Pro Asn Asn Asn Thr Arg Lys Ser Val Arg Ile Gly Pro
1               5                   10                  15

Gly Gln Ala Phe Tyr Ala Thr Gly Asp Ile Ile Gly Asp Ile Arg Gln
            20                  25                  30

Ala His Cys
        35

<210> SEQ ID NO 49
<211> LENGTH: 35
<212> TYPE: PRT
<213> ORGANISM: Human immunodeficiency virus

<400> SEQUENCE: 49

Cys Val Arg Pro Ser Asn Asn Thr Arg Lys Ser Ile Arg Ile Gly Pro
1               5                   10                  15

Gly Gln Thr Phe Tyr Ala Thr Gly Asp Ile Thr Gly Asp Ile Arg Gln
            20                  25                  30

Ala His Cys
        35

<210> SEQ ID NO 50
<211> LENGTH: 34
<212> TYPE: PRT
<213> ORGANISM: Human immunodeficiency virus

<400> SEQUENCE: 50

Cys Thr Arg Pro Ser Asn Asn Thr Arg Gln Gly Ile His Ile Gly Pro
1               5                   10                  15

Gly Gln Ala Leu Tyr Thr Thr Lys Ile Ile Gly Asp Ile Arg Gln Ala
            20                  25                  30

His Cys

<210> SEQ ID NO 51
<211> LENGTH: 35
<212> TYPE: PRT
<213> ORGANISM: Human immunodeficiency virus

<400> SEQUENCE: 51

Cys Thr Arg Pro Asn Asn Asn Thr Arg Lys Ser Ile His Ile Gly Pro

```
                1               5                  10                 15
Gly Gln Ala Phe Tyr Ala Ile Gly Asp Val Ile Gly Asn Ile Arg Gln
                20                 25                 30

Ala Gln Cys
        35

<210> SEQ ID NO 52
<211> LENGTH: 35
<212> TYPE: PRT
<213> ORGANISM: Human immunodeficiency virus

<400> SEQUENCE: 52

Cys Ile Arg Pro Asn Asn Asn Thr Arg Lys Ser Val His Ile Gly Pro
1               5                  10                 15

Gly Gln Thr Phe Tyr Ala Thr Gly Asp Ile Ile Gly Asn Ile Arg Gln
                20                 25                 30

Ala His Cys
        35

<210> SEQ ID NO 53
<211> LENGTH: 38
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (10)..(11)
<223> OTHER INFORMATION: The Xaa at positions 10-11 can be any amino
      acid
<220> FEATURE:
<221> NAME/KEY: MISC_FEATURE
<222> LOCATION: (14)..(15)
<223> OTHER INFORMATION: The Xaa at positions 14-15 can be any amino
      acid
<220> FEATURE:
<221> NAME/KEY: MISC_FEATURE
<222> LOCATION: (21)..(21)
<223> OTHER INFORMATION: The Xaa at position 21 can be any amino acid
<220> FEATURE:
<221> NAME/KEY: MISC_FEATURE
<222> LOCATION: (23)..(23)
<223> OTHER INFORMATION: The Xaa at position 23 can be any amino acid
<220> FEATURE:
<221> NAME/KEY: MISC_FEATURE
<222> LOCATION: (26)..(26)
<223> OTHER INFORMATION: The Xaa at position 26 can be any amino acid
<220> FEATURE:
<221> NAME/KEY: MISC_FEATURE
<222> LOCATION: (28)..(30)
<223> OTHER INFORMATION: The Xaa at positions 28-30 can be any amino
      acid
<220> FEATURE:
<221> NAME/KEY: MISC_FEATURE
<222> LOCATION: (34)..(35)
<223> OTHER INFORMATION: The Xaa at positions 34-35 can be any amino
      acid
<220> FEATURE:
<221> NAME/KEY: MISC_FEATURE
<222> LOCATION: (37)..(37)
<223> OTHER INFORMATION: The Xaa at position 37 can be any amino acid

<400> SEQUENCE: 53

Cys Thr Arg Pro Asn Asn Asn Thr Arg Xaa Xaa Arg Ile Xaa Xaa Gly
1               5                  10                 15

Pro Gly Arg Ala Xaa Tyr Xaa Thr Gly Xaa Ile Xaa Xaa Xaa Gly Asp
                20                 25                 30

Ile Xaa Xaa Ala Xaa Cys
        35
```

-continued

<210> SEQ ID NO 54
<211> LENGTH: 35
<212> TYPE: PRT
<213> ORGANISM: Human immunodeficiency virus

<400> SEQUENCE: 54

Cys Thr Arg Pro Asn Asn Asn Thr Arg Lys Arg Ile His Ile Gly Pro
1               5                   10                  15

Gly Arg Ala Phe Tyr Thr Thr Gly Gln Ile Ile Gly Asn Ile Arg Gln
            20                  25                  30

Ala Tyr Cys
        35

<210> SEQ ID NO 55
<211> LENGTH: 35
<212> TYPE: PRT
<213> ORGANISM: Human immunodeficiency virus

<400> SEQUENCE: 55

Cys Thr Arg Pro Asn Asn Asn Thr Arg Lys Arg Ile His Ile Gly Pro
1               5                   10                  15

Gly Arg Ala Phe Tyr Thr Thr Gly Gln Ile Ile Gly Asn Ile Arg Gln
            20                  25                  30

Ala His Cys
        35

<210> SEQ ID NO 56
<211> LENGTH: 35
<212> TYPE: PRT
<213> ORGANISM: Human immunodeficiency virus

<400> SEQUENCE: 56

Cys Thr Arg Pro Asn Asn Asn Thr Arg Lys Arg Ile His Ile Gly Pro
1               5                   10                  15

Gly Arg Ala Phe His Thr Thr Gly Ala Ile Ile Gly Lys Ile Arg Gln
            20                  25                  30

Ala His Cys
        35

<210> SEQ ID NO 57
<211> LENGTH: 35
<212> TYPE: PRT
<213> ORGANISM: Human immunodeficiency virus

<400> SEQUENCE: 57

Cys Thr Arg Pro Asn Asn Asn Thr Arg Lys Arg Ile His Ile Gly Pro
1               5                   10                  15

Gly Arg Ala Phe Tyr Thr Thr Gly Gly Ile Ile Gly Asn Ile Arg Gln
            20                  25                  30

Ala His Cys
        35

<210> SEQ ID NO 58
<211> LENGTH: 35
<212> TYPE: PRT
<213> ORGANISM: Human immunodeficiency virus

<400> SEQUENCE: 58

Cys Thr Arg Pro Asn Asn Asn Thr Arg Lys Arg Ile His Ile Gly Pro
1               5                   10                  15

-continued

```
Gly Arg Ala Phe Tyr Ala Thr Gly Lys Ile Ile Gly Asp Ile Arg Gln
            20                  25                  30

Ala His Cys
        35

<210> SEQ ID NO 59
<211> LENGTH: 35
<212> TYPE: PRT
<213> ORGANISM: Human immunodeficiency virus

<400> SEQUENCE: 59

Cys Ile Arg Pro Asn Asn Asn Thr Arg Arg Ile His Ile Gly Pro
1               5                   10                  15

Gly Arg Ala Phe Tyr Ala Thr Gly Arg Ile Ile Gly Asn Ile Arg Gln
            20                  25                  30

Ala Tyr Cys
        35

<210> SEQ ID NO 60
<211> LENGTH: 35
<212> TYPE: PRT
<213> ORGANISM: Human immunodeficiency virus

<400> SEQUENCE: 60

Cys Ile Arg Pro Asn Asn Asn Thr Arg Arg Ser Ile His Ile Gly Pro
1               5                   10                  15

Gly Arg Ala Phe Tyr Ala Thr Gly Arg Ile Ile Gly Asp Ile Arg Arg
            20                  25                  30

Ala Tyr Cys
        35

<210> SEQ ID NO 61
<211> LENGTH: 35
<212> TYPE: PRT
<213> ORGANISM: Human immunodeficiency virus

<400> SEQUENCE: 61

Cys Ile Arg Pro Asn Asn Asn Thr Arg Thr Lys Ile Arg Ile Gly Pro
1               5                   10                  15

Gly Gln Ala Phe Tyr Ala Thr Gly Asn Ile Ile Gly Asp Ile Arg Gln
            20                  25                  30

Ala Tyr Cys
        35

<210> SEQ ID NO 62
<211> LENGTH: 35
<212> TYPE: PRT
<213> ORGANISM: Human immunodeficiency virus

<400> SEQUENCE: 62

Cys Leu Arg Pro Asn Asn Asn Thr Arg Lys Arg Ile His Leu Gly Pro
1               5                   10                  15

Gly Arg Ala Phe Tyr Ala Ala Gly Glu Ile Ile Gly Lys Ile Arg Gln
            20                  25                  30

Ala His Cys
        35

<210> SEQ ID NO 63
<211> LENGTH: 35
<212> TYPE: PRT
```

-continued

<213> ORGANISM: Human immunodeficiency virus

<400> SEQUENCE: 63

Cys Thr Arg Pro Asn Asn Asn Ile Arg Arg Arg Ile His Ile Gly Pro
1               5                   10                  15

Gly Arg Ala Phe Tyr Ala Thr Gly Asp Ile Ile Gly Asp Ile Arg Lys
            20                  25                  30

Ala Tyr Cys
        35

<210> SEQ ID NO 64
<211> LENGTH: 35
<212> TYPE: PRT
<213> ORGANISM: Human immunodeficiency virus

<400> SEQUENCE: 64

Cys Thr Arg Pro Asn Asn Asn Thr Arg Arg Arg Ile His Ile Gly Pro
1               5                   10                  15

Gly Arg Ala Phe Tyr Ala Thr Gly Asp Thr Ile Gly Asp Ile Arg Lys
            20                  25                  30

Ala Tyr Cys
        35

<210> SEQ ID NO 65
<211> LENGTH: 35
<212> TYPE: PRT
<213> ORGANISM: Human immunodeficiency virus

<400> SEQUENCE: 65

Cys Thr Arg Pro Asn Asp Asn Ile Arg Lys Arg Val His Ile Gly Pro
1               5                   10                  15

Gly Gln Ala Phe Tyr Ala Thr Gly Asp Val Ile Gly Asp Ile Arg Arg
            20                  25                  30

Ala His Cys
        35

<210> SEQ ID NO 66
<211> LENGTH: 35
<212> TYPE: PRT
<213> ORGANISM: Human immunodeficiency virus

<400> SEQUENCE: 66

Cys Thr Arg Pro Asn Asn Asn Ile Arg Arg Arg Ile His Ile Gly Pro
1               5                   10                  15

Gly Arg Ala Phe Tyr Ala Thr Gly Gly Ile Arg Gly Asp Ile Arg Lys
            20                  25                  30

Ala Tyr Cys
        35

<210> SEQ ID NO 67
<211> LENGTH: 35
<212> TYPE: PRT
<213> ORGANISM: Human immunodeficiency virus

<400> SEQUENCE: 67

Cys Thr Arg Pro Asn Asn Asn Ile Arg Arg Arg Ile Arg Ile Gly Pro
1               5                   10                  15

Gly Arg Ala Tyr Phe Thr Arg Gly Gln Ile Lys Glu His Met Arg Lys
            20                  25                  30

Ala His Cys

-continued

```
                35

<210> SEQ ID NO 68
<211> LENGTH: 35
<212> TYPE: PRT
<213> ORGANISM: Human immunodeficiency virus

<400> SEQUENCE: 68

Cys Thr Arg Pro Ser Asn Asn Thr Arg Lys Arg Ile Pro Ile Gly Pro
1               5                   10                  15

Arg Arg Ala Phe Tyr Ala Thr Gly Asp Ile Val Gly Asp Ile Arg Arg
            20                  25                  30

Ala His Cys
        35

<210> SEQ ID NO 69
<211> LENGTH: 35
<212> TYPE: PRT
<213> ORGANISM: Human immunodeficiency virus

<400> SEQUENCE: 69

Cys Thr Arg Pro Asn Asn His Thr Arg Lys Arg Met Thr Leu Gly Pro
1               5                   10                  15

Gly Arg Val Tyr Tyr Thr Thr Gly Glu Ile Leu Gly Asp Ile Lys Lys
            20                  25                  30

Ala His Cys
        35

<210> SEQ ID NO 70
<211> LENGTH: 35
<212> TYPE: PRT
<213> ORGANISM: Human immunodeficiency virus

<400> SEQUENCE: 70

Cys Thr Arg Pro Asn Asn His Thr Arg Lys Arg Met Thr Leu Gly Pro
1               5                   10                  15

Gly Lys Val Tyr Tyr Thr Thr Gly Glu Ile Val Gly Asp Ile Lys Lys
            20                  25                  30

Ala His Cys
        35

<210> SEQ ID NO 71
<211> LENGTH: 35
<212> TYPE: PRT
<213> ORGANISM: Human immunodeficiency virus

<400> SEQUENCE: 71

Cys Thr Arg Pro Asn Asn His Thr Arg Lys Arg Ile Ser Leu Gly Pro
1               5                   10                  15

Gly Arg Ala Tyr Tyr Thr Thr Gly Glu Ile Val Gly Ser Ile Lys Lys
            20                  25                  30

Ala His Cys
        35

<210> SEQ ID NO 72
<211> LENGTH: 35
<212> TYPE: PRT
<213> ORGANISM: Human immunodeficiency virus

<400> SEQUENCE: 72

Cys Thr Arg Pro Asn Asn Asn Thr Arg Lys Arg Ile Arg Ile Gly Pro
```

```
                1               5                  10                 15
Gly Arg Ala Val Tyr Thr Thr Gly Lys Ile Ile Gly Lys Ile Arg Gln
            20                  25                 30

Ala His Cys
        35

<210> SEQ ID NO 73
<211> LENGTH: 35
<212> TYPE: PRT
<213> ORGANISM: Human immunodeficiency virus

<400> SEQUENCE: 73

Cys Thr Arg Pro Asn Thr Asn Lys Arg Lys Arg Thr Thr Lys Gly Pro
1               5                  10                 15

Gly Arg Val Ile Tyr Ala Thr Gly Gln Ile Ile Gly Lys Ile Arg Gln
            20                  25                 30

Ala His Cys
        35

<210> SEQ ID NO 74
<211> LENGTH: 35
<212> TYPE: PRT
<213> ORGANISM: Human immunodeficiency virus

<400> SEQUENCE: 74

Cys Thr Arg Pro Asn Asn Asn Thr Arg Lys Arg Ile Ser Ile Gly Pro
1               5                  10                 15

Gly Arg Ala Phe Tyr Thr Thr Gly Gln Ile Ile Gly Asn Ile Arg Gln
            20                  25                 30

```
<212> TYPE: PRT
<213> ORGANISM: Human immunodeficiency virus

<400> SEQUENCE: 77

Cys Thr Arg Pro Lys Asn Asn Thr Arg Lys Pro Ile His Ile Gly Pro
1               5                   10                  15

Gly Arg Ala Phe Tyr Ala Thr Arg Glu Ile Arg Gly Asn Ile Ile Gln
            20                  25                  30

Ala His Cys
        35

<210> SEQ ID NO 78
<211> LENGTH: 35
<212> TYPE: PRT
<213> ORGANISM: Human immunodeficiency virus

<400> SEQUENCE: 78

Cys Thr Arg Pro Asn Asn Asn Thr Arg Lys Arg Ile Ser Val Gly Pro
1               5                   10                  15

Gly Arg Ala Phe Tyr Ala Thr Gly Asn Ile Ile Gly Lys Ile Ser Gln
            20                  25                  30

Ala His Cys
        35

<210> SEQ ID NO 79
<211> LENGTH: 35
<212> TYPE: PRT
<213> ORGANISM: Human immunodeficiency virus

<400> SEQUENCE: 79

Cys Thr Arg Pro Asn Asn Asn Thr Arg Lys Arg Ile Arg Ile Gly Pro
1               5                   10                  15

Gly Arg Ala Phe Tyr Thr Thr Gly Gln Ile Ile Gly Asp Ile Arg Gln
            20                  25                  30

Ala His Cys
        35

<210> SEQ ID NO 80
<211> LENGTH: 35
<212> TYPE: PRT
<213> ORGANISM: Human immunodeficiency virus

<400> SEQUENCE: 80

Cys Thr Arg Pro Asn Asn Asn Thr Ile Thr Arg Ile Arg Ile Gly Pro
1               5                   10                  15

Gly Gln Ala Phe Tyr Ala Thr Gly Ser Ile Ile Gly Asn Ile Arg Gln
            20                  25                  30

Ala His Cys
        35

<210> SEQ ID NO 81
<211> LENGTH: 37
<212> TYPE: PRT
<213> ORGANISM: Human immunodeficiency virus

<400> SEQUENCE: 81

Cys Ser Arg Pro Tyr Lys Lys Glu Arg Gln Arg Thr His Ile Gly Pro
1               5                   10                  15

Gly Gln Ala Leu Tyr Thr Thr Arg Thr Thr Arg Val Glu Gly Asn Ile
            20                  25                  30
```

```
                               -continued

Arg Gln Ala His Cys
        35

<210> SEQ ID NO 82
<211> LENGTH: 35
<212> TYPE: PRT
<213> ORGANISM: Human immunodeficiency virus

<400> SEQUENCE: 82

Cys Val Arg Pro Tyr Arg Asn Ile Lys Ile Gln Arg Thr Pro Ile Gly
1               5                   10                  15

Leu Gly Gln Ala Leu Tyr Thr Lys Arg Ile Gly His Ile Gly Gln
            20                  25                  30

Ala His Cys
        35
```